US012051501B2

(12) United States Patent
Diggett et al.

(10) Patent No.: US 12,051,501 B2
(45) Date of Patent: Jul. 30, 2024

(54) PASSIVE ALARM STATE ADJUSTMENT

(71) Applicant: CareFusion 303, Inc., San Diego, CA (US)

(72) Inventors: Lisa Diggett, Overland Park, KS (US); Laura Ann Collins, Collierville, TN (US); Claire Ellen Knight, Arlington, TX (US); Michael K Workman, Carlsbad, CA (US)

(73) Assignee: CareFusion 303, Inc., San Diego, CA (US)

( * ) Notice: Subject to any disclaimer, the term of this patent is extended or adjusted under 35 U.S.C. 154(b) by 329 days.

(21) Appl. No.: 17/530,391

(22) Filed: Nov. 18, 2021

(65) Prior Publication Data
US 2022/0165405 A1 May 26, 2022

Related U.S. Application Data

(60) Provisional application No. 63/116,758, filed on Nov. 20, 2020.

(51) Int. Cl.
*G16H 40/63* (2018.01)
*G06F 3/16* (2006.01)
(Continued)

(52) U.S. Cl.
CPC ............ *G16H 40/63* (2018.01); *G06F 3/165* (2013.01); *G06F 21/31* (2013.01); *G08B 7/06* (2013.01); *H04R 3/00* (2013.01); *H04R 2430/01* (2013.01)

(58) Field of Classification Search
CPC ......... G16H 40/63; G06F 3/165; G06F 21/31; G08B 7/06; H04R 3/00; H04R 2430/01
(Continued)

(56) References Cited

U.S. PATENT DOCUMENTS 5,681,285 A    10/1997 Ford et al.
5,713,856 A    2/1998 Eggers et al.
(Continued)

OTHER PUBLICATIONS

International Search Report and Written Opinion for Application No. PCT/US2021/060042, dated Mar. 4, 2022, 16 pages.
(Continued)

*Primary Examiner* — Kam Wan Ma
(74) *Attorney, Agent, or Firm* — Morgan, Lewis & Bockius LLP

(57) ABSTRACT

The disclosed systems and methods for reducing alarm strain generated by a medical device. A medical device for reducing generated alarm strain includes a display to present visually perceivable information, an audio output to present audibly perceivable information, processors coupled with the display and the audio output, and memory storing instructions that, when executed by the processors, cause the medical device to perform operations. The instructions, when executed, cause the medical device to receive a notification regarding the medical device. The notification is associated with an audible manifestation and a visual manifestation. The instructions, when executed, also cause the medical device to detect that a user is focused on the medical device, after said detection of the user, determine a volume adjustment to the audio output for presenting the audible manifestation, and adjust the audio output to cause presentation of the audible manifestations according to the volume adjustment.

19 Claims, 10 Drawing Sheets

(51) Int. Cl.
    *G06F 21/31*    (2013.01)
    *G08B 7/06*     (2006.01)
    *H04R 3/00*     (2006.01)

(58) Field of Classification Search
    USPC ........................................................ 340/506
    See application file for complete search history.

(56) References Cited

U.S. PATENT DOCUMENTS

| | | | |
|---|---|---|---|
| 9,911,313 B2 | 3/2018 | Kelly et al. | |
| 2007/0040692 A1* | 2/2007 | Smith | A61B 5/1115 340/573.1 |
| 2008/0281168 A1* | 11/2008 | Gibson | A61B 5/002 600/301 |
| 2014/0135588 A1 | 5/2014 | Al-Ali et al. | |
| 2014/0288947 A1* | 9/2014 | Simpson | G16H 40/67 705/2 |

OTHER PUBLICATIONS

Qiu et al., "A survey of machine learning for big data processing", EURASIP Journal Advances in Signal Processing, May 28, 2016, Article No. 67 (2016), https://doi.org/10.1186/s13634-016-0355-x.

* cited by examiner

PASSIVE ALARM STATE ADJUSTMENT

CROSS-REFERENCE TO RELATED APPLICATION(S)

This application claims priority to and is a non-provisional of U.S. Provisional Application Ser. No. 63/116,758, entitled "PASSIVE ALARM STATE ADJUSTMENT," filed on Nov. 20, 2020, the entirety of which is incorporated herein by reference.

TECHNICAL FIELD

The present disclosure generally relates to alarms, and more specifically relates to methods and systems for passively adjusting alarm states of a medical device to reduce alarm strain without compromising patient safety.

BACKGROUND

Patients at a hospital, medical clinic, and/or healthcare facilities often receive treatment via one or more medical device. To ensure that the medical devices are operating properly and/or if additional attention is needed, the medical devices generate several alarms, alerts, and/or other notifications. At a healthcare facility, several medical devices can be used at a time and/or a medical device can generate multiple notifications. The constant alarms, alerts, and notifications generate additional stress for patients and clinicians. The problem is further worsened when multiple medical devices are in the same room on the same floor and/or even in the same building. As such, a way of easing the generated alarm strain by medical devices is needed.

SUMMARY

According to various implementations, a method for reducing alarm strain is provided. The method may include, at a medical device, receiving a notification regarding the medical device, wherein the notification is associated with at least two human perceivable manifestations. The method includes, at the medical device, detecting that a user is focused on the medical device such as by authenticating the user to the medical device or detecting an interaction (e.g., touchscreen or button input) via the medical device. The method may further include adjusting presentation, by the medical device, of at least one of the human perceivable manifestations of the notification for a predetermined period of time, said adjusting based at least in part on said detecting. In some implementations, adjusting presentation, by the medical device, of the at least one of the human perceivable manifestations of the notification for the predetermined period of time includes silencing an audible manifestation of the notification and/or temporarily dismissing a visual manifestation of the notification.

In some implementations, detecting that the user is focused on the medical device includes detecting a user identifier in proximity to the medical device, and automatically receiving credentials of the user via an electronic device associated with the user. More specifically, detecting the user identifier in proximity to the medical device includes a one-foot detection radius around the medical device. In some implementations, being in proximity to the medical device includes making contact with the medical device. In some implementations, being in proximity to the medical device includes being within 1 ft. of the medical device.

In some implementations, the method includes presenting, at the medical device, at least one human perceivable manifestations of another notification to the user. The at least one human perceivable manifestation of the other notification is generated by a distinct medical device associated with the user. In some implementation, the distinct medical device is in proximity to the medical device, and in response to the determination that the authentication request was received from the user, the method includes adjusting presentation of the at least one human perceivable manifestations of the other notification for the predetermined period of time.

In some implementations, the predetermined period of time is at least 30 seconds. In some implementations, the predetermined period of time is dynamically determined. For example, in some implementations. The medical device is an infusion pump, and the method includes dynamically determining the predetermined period of time based, in part, on a drug being infused, alarm type, user preference, whether user is logged into the infusion pump, whether infusion pump is locked, and/or user proximity to the infusion pump.

In some implementations, the method includes disabling a silence notification feature of the medical device, wherein activation of the silence notification feature adjusts a manifestation of the notification generated by the medical device. Disabling the silence notification feature may include hiding a control element on a user interface of the medical device or suppressing signals received from an electromechanical input of the medical device. Upon authentication of the user, the silence notification feature may be enabled. The silent notification feature may be enabled for a predetermined period of time or until the medical device detects the user's focus is no longer on the medical device such as by detecting a log-off or no longer detecting a user authentication device within the proximity of the medical device.

In some implementations, adjusting a manifestation of the notification may include detecting an environmental condition within proximity of the medical device. The environmental condition may include time, light level, noise level, temperature, number of pumping modules associated with the medical device, patient information, patient monitoring data, medical device location (e.g., care area), or the like. The adjusting additionally or alternatively may be based on the detected environmental conditions.

In some implementations, adjusting a manifestation of the notification may include retrieving a user notification configuration from a data storage device. The retrieval may be based at least in part on a portion of authentication information received by the medical device for the user. The user notification configuration may include color pallet, audio tone, audio rate, audio pitch, or similar values to adjust presentation of a manifestation. The adjusting additionally or alternatively may be based on the user notification configuration received.

In accordance with various implementations, a medical device for reducing generated alarm strain is provided. The medical device includes a display to present visually perceivable information, an audio output to present audibly perceivable information, one or more processors coupled with the display and the audio output, and memory storing one or more instructions. The one or more instructions, when executed by the one or more processors, cause the medical device to perform operations including receive a notification regarding the medical device. The notification is associated with an audible manifestation and a visual manifestation. The one or more instructions, when executed by the one or more processors, cause the medical device to detect that a user is focused on the medical device. Detecting that the user is focused on the medical device is based on authenticating the user to the medical device or detecting user interaction via the medical device. The one or more instructions, when executed by the one or more processors, further cause the medical device to, after said detection of the user, determine a volume adjustment to the audio output for presenting the audible manifestation and adjust the audio output to cause presentation of the audible manifestations according to the volume adjustment. The audio output presents the audible manifestation with the volume adjustment at a lower volume than the audio output would present the audible manifestation without the volume adjustment.

In accordance with various implementations, anon-transitory computer readable medium storing one or more programs, the one or more programs including instructions, which when executed by a medical device, cause the medical device to receive a notification regarding the medical device. The notification is associated with at least two human perceivable manifestations. The one or more programs further include instructions, which when executed by the medical device, cause the medical device to detect that a user is focused on the medical device. Detecting that the user is focused on the medical device is based on authenticating the user to the medical device or detecting user interaction via the medical device. The one or more programs further include instructions, which when executed by the medical device, cause the medical device to determine one or more adjustments to at least one of the human perceivable manifestation of the notification, a determined one or more adjustments based at least in part on said detecting, and adjust presentation of the at least one of the human perceivable manifestations of the notification for a predetermined period of time. The adjusted presentation based at least in part on the determined one or more adjustments.

In some implementations, adjusting presentation, by the medical device, of the at least one of the human perceivable manifestations of the notification for the predetermined period of time includes silencing an audible manifestation of the notification and/or temporarily dismissing a visual manifestation of the notification. In some implementations, detecting that the user is focused on the medical device includes detecting a user identifier in proximity to the medical device, and automatically receiving credentials of the user via an electronic device associated with the user.

In some implementations, one or more programs further include instructions, which when executed by a medical device, cause the medical device to detect an environmental condition within proximity of the medical device and the determined one or more adjustments are based at least in part on a detected environmental condition. In some implementations, one or more programs further include instructions, which when executed by a medical device, cause the medical device to retrieve a user notification configuration from a data storage device, wherein the retrieval is based at least in part on a portion of authentication information received by the medical device for the user. The determined one or more adjustments are based at least in part on the user notification configuration.

In some implementations, one or more programs further include instructions, which when executed by a medical device, cause the medical device to activate a control element of the medical device for acknowledging the notification, said activation of the control element based at least in part on said detecting and upon activation of the control element, adjust the presentation of the at least one of the human perceivable manifestations of the notification.

In some implementations, one or more programs further include instructions, which when executed by a medical device, cause the medical device to receive a parameter to control delivery of a fluid via the medical device, and wherein the user interaction includes receiving the parameter.

Other aspects include corresponding systems, apparatuses, and computer program products for implementation of the computer-implemented method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

DESCRIPTION

Figure 1:
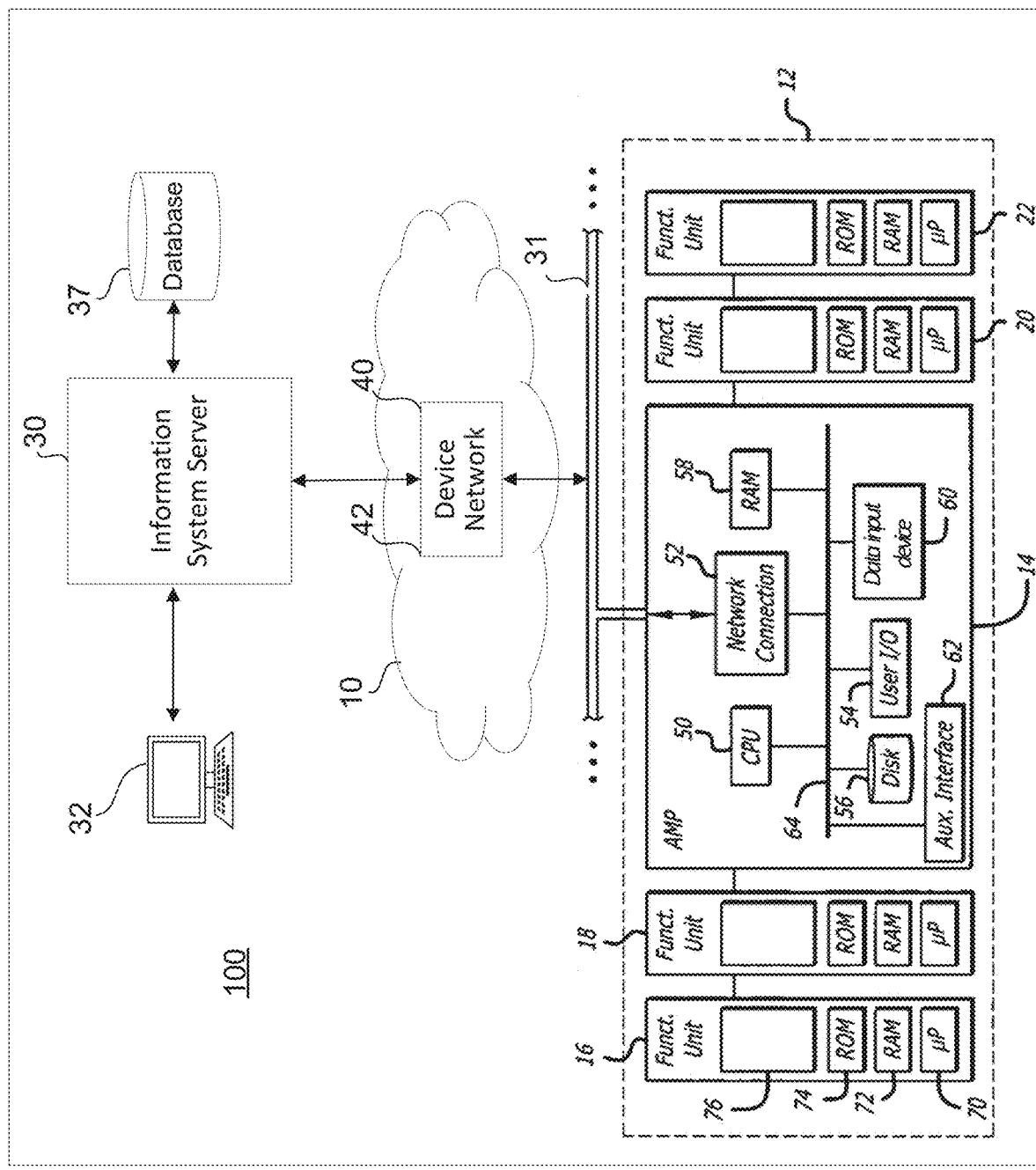
FIG. 1 depicts an example of an institutional patient care system of a healthcare organization, according to various aspects of the subject technology.

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The subject technology includes a system and method for passively (e.g., without express intent by a user) adjusting (e.g., silencing or temporarily dismissing) one or more human perceivable manifestations of alarms, alerts, or notifications generated and presented by medical devices. For purposes of this disclosure, alarms, alerts, or notifications are generally referred to as "notifications." An existing point-of-care unit may constantly generate notifications that can cause stress and strain to patients and clinicians. Additionally, some systems include specific silence buttons or other control elements that can be deliberately activated (e.g., with express intent by a user) to adjust the notification manifestations. In some instances, an unauthorized user (such as a family member or other visitor of the patient) may activate the silence control element. While well intentioned, silencing notifications can delay identification of a safety issue to a clinician caring for the patient.

Further, many point-of-care units can be located in proximity to each other, associated with a single patient, and/or associated with a single clinician, which add to the total number of generated notifications. When a user first accesses a medical device that is presenting a notification, the medical device adjusts (e.g., silences and/or dismisses) at least one manifestation of the notification for a notification suppression period. The notification suppression period may be a statically or dynamically predetermined period of time during which the manifestation is adjusted.

Additionally or alternatively, the way a notification is manifested can cause different responses by the clinician or the patient. For example, if a clinician is color blind or otherwise visually impaired, selection of color palates or fonts (e.g., style, size) for presenting visual notifications can influence their ability to perceive the notification. As another example, a clinician or patient may have hearing that cannot detect certain audio tones, frequencies, pitches, etc. In some cases, even if the audio is detectable, the audio characteristic for a manifestation may be unpleasant (e.g., sour sounding, offensive, psychologically triggering). In this way, the medical device includes features to efficiently reduce or eliminate additional alarm strain until the user is able to attend to the notification.

FIG. 1 depicts an example of an institutional patient care system 100 of a healthcare organization, according to aspects of the subject technology. In FIG. 1, a patient care device (or "medical device" generally) 12 is connected to a hospital network 10. The term patient care device (or "PCD") may be used interchangeably with the term point-of-care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which PCDs 12 (and other devices) communicate in accordance with normal operations.

Additionally, institutional patient care system 100 may incorporate a separate information system server 30, the function of which will be described in more detail below. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, and mobile devices such as laptops, tablet computers, augmented reality devices, or smartphones, configured with software for communications with information system server 30 via network 10.

PCD 12 comprises a system for providing patient care, such as that described in U.S. Pat. No. 5,713,856 to Eggers et al., which is incorporated herein by reference for that purpose. PCD 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, PCD 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54 (e.g., a display screen and/or keyboard), a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to PCD 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

PCD 12 is capable of operating in several different modes, or personalities, with each personality defined by a configuration database. Each mode or personality may include a different set of configuration parameters, or implement a different drug library, as described below. The configuration database may be a database 56 internal to PCD 12, or an external database 37. A particular configuration database (or portion thereof) may be selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a PCD 12's location in the hospital or hospital computer network. Patient care information may be entered through interface device 52, 54, 60 or 62, and may have originated from anywhere in network 10, such as, for example, from a pharmacy server, admissions server, laboratory server, and the like.

In some implementations, the database 56 internal to the PCD 12, and/or the external database 37 includes clinician data. The clinician data includes clinician account information, clinician association with one or more PCDs 12 and/or patients, clinician preference, and/or other relevant clinician information. The clinician account information includes a unique identifier for each clinician (or other authorized user) and respective authentication information (e.g., credentials, authentication tokens, passwords, authenticated biometric information, etc.) such that the clinician can access PCDs 12 they are associated with. The clinician preferences include configurations for manifestation of notifications, such as clinician specific visual manifestations of notifications (e.g., colors, flashes, font (e.g., size and/or style), banners, backgrounds, background effects, overlays, and/or other visual effects), clinician specific audio manifestations of notifications (e.g., volume, tone, pitch, patterns, and/or rate), other clinician specific human perceivable manifestations of notifications (e.g., haptic feedback, vibrations, etc.), and/or accommodations for clinician disabilities and/or impairments (e.g., color blindness, hearing loss, deafness, blindness, etc.). In some implementations, the clinician data includes clinician interaction with a PCD 12. A non-exhaustive list of clinician interaction with a PCD 12 includes client response times to notification manifestations (or lack thereof), inputs provided to the PCDs 12 (and/or functional models 16, 18, 20, 22), current and past programming configurations, interactions with other networked PCDs 12, etc. In some implementations, the clinician interaction with a PCD 12 is used to determine one or more manifestations of notifications for the clinician as well as adjustments to the manifestations.

In some implementations, the database 56 internal to the PCD 12, and/or the external database 37 includes patient specific configuration data for the manifestations of notifications. The patient specific configurations include patient specific visual manifestation of notifications, patient specific audio manifestations of notifications, other patient specific human perceivable manifestations of notifications, and/or accommodations for patient conditions or illnesses (e.g., light sensitivity, audio sensitivity, sleep patterns, etc.). In particular, the patient specific configurations can define, for a patient, manifestations of notifications and adjustments for the manifestations of notifications such that a clinician can easily identify the patient and/or to assign a patient with manifestations of notifications that cause the least amount stress or strain to the patient. For example, a patient with light sensitivity may not have manifestations of notifications with continuous flashes or bright lights.

In some implementations, the database 56 internal to the PCD 12, and/or the external database 37 includes PCD 12 specific data for the manifestations of notifications. The PCD 12 specific data includes information corresponding to one or more components (e.g., speakers, displays, illuminating devices (e.g., LEDs), haptic devices, etc.) of the PCD 12 and/or manifestations of the notifications that the PCD 12 is capable of presenting. For example, the PCD 12 specific data can indicate that the PCD 12 does not have any audio outputs (e.g., speakers) and therefore cannot present audio manifestations of the notification. Alternatively, the PCD 12 specific data can indicate that the PCD 12 is in communication with at least one functional model 16, 18, 20, 22 that includes a speaker and the PCD 12 can be configured to present the audio manifestations of the notification via the functional model's speaker. In this way, the PCD 12 is able to adjust the manifestations of the notifications within the limits of its configuration. In some implementations, the PCD 12 specific data includes time and date information as well as information on other environmental conditions (e.g., surrounding sounds, current lighting, temperature, etc.), which are used to determine one or more manifestations of the notifications and adjustments thereof (e.g., adjustments to manifestations for night, early morning, loud rooms, etc.). In some implementations, the PCD 12 specific data includes location data, which is used to determine one or more manifestations of the notifications and adjustments thereof. For example, the PCD 12 can use its location data in conjunction with the location data of other PCDs 12 to determine one or more adjustments to the manifestations of the notifications such that additional manifestations of notifications do not significantly increase the generated alarm stress and strain.

In some implementations, the PCD 12, and/or the external database 37 includes manifestation data for configuring the notifications. The manifestation data includes visual and/or audio adjustments for manifestations of notifications, which are configured to comply with the standards set for in IEC 60601.

A controller 14 of PCD 12 also has access to a drug library. Further information on drug libraries is contained in U.S. Pat. No. 5,681,285 to Ford, which is incorporated herein by reference in its entirety. The drug library may be resident in the controller, in a local accessible memory, or may be located elsewhere on the system network but be accessible by the controller. "Drug Library Profiles" may be established in which medications (e.g., drugs), concentrations, and other pumping parameters are set particular to that care area—such as, for example, an ICU (intensive care unit) profile, a pediatric profile, a neonatal profile, and others. Data sets of medications allowed for use and configurations of pumping parameters including limitations for that use may be available for each drug library profile. As such, drug library profiles may, although not necessarily, correspond to different patient care areas of the hospital. Thus, a controller 14 located in a pediatric ward, for example, may utilize a pediatric drug library profile that includes sets of allowed medications, pumping parameters, and pumping limitations that are specific to patients classified as pediatric or located in a pediatric ward. Similarly, a controller 14 located in an ICU may utilize an ICU drug library profile that includes a different set of allowed medications, pumping parameters, and pumping limitations that are specific to patients located in an intensive care environment and other patients requiring intensive care Medical devices incorporating aspects of the subject technology may be equipped with a Network Interface Module (MM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, PCD 12 and network 10 may communicate via automated interaction, manual interaction, or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between PCD 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within PCD 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figure 2:
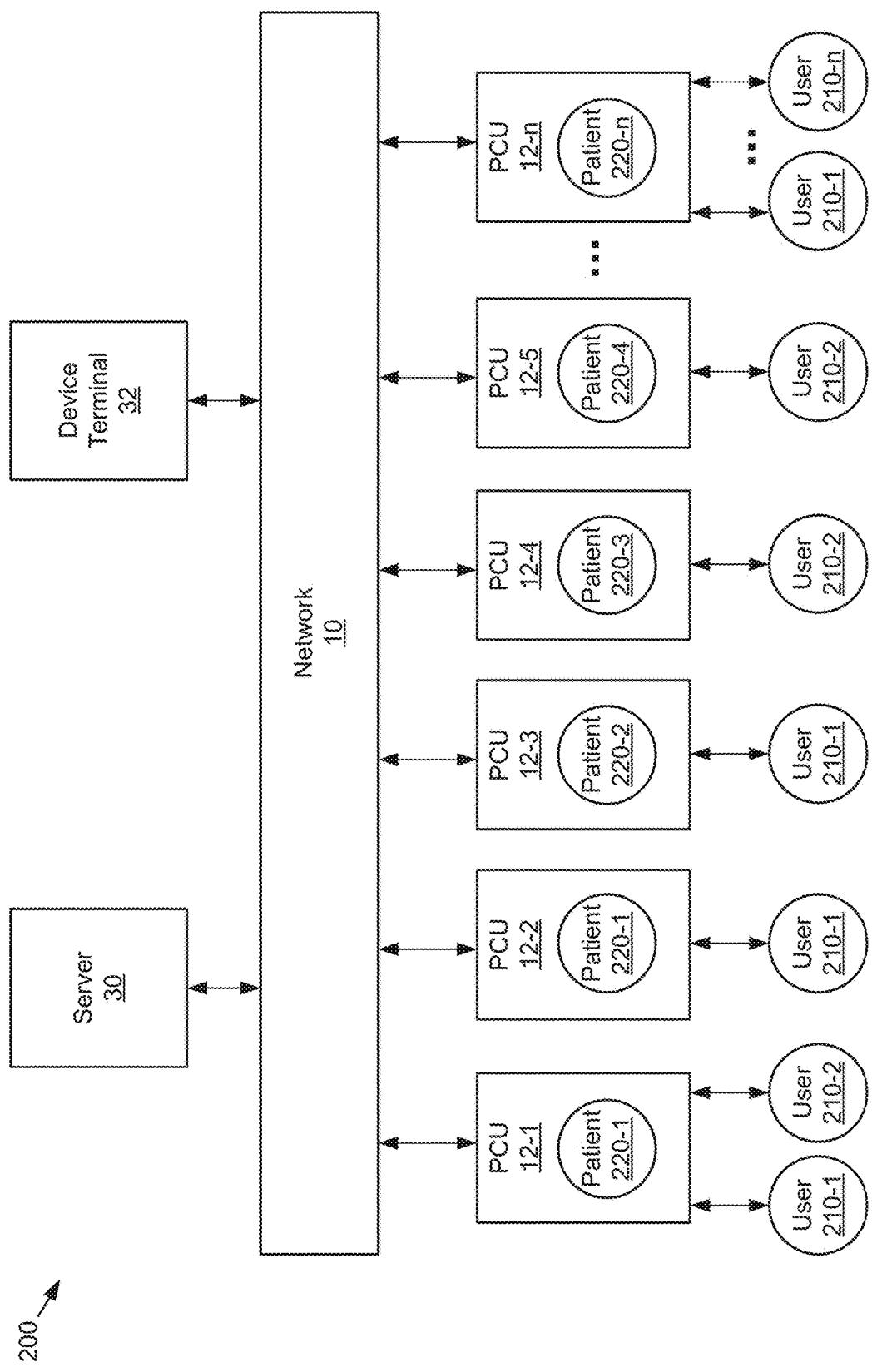
FIG. 2 illustrates an overview of a network of point-of-care units, according to various aspects of the subject technology.

FIG. 2 illustrates a system overview of networked PCDs, in accordance with some implementations. The system 200 includes a network 10, server 30, one or more device terminals 32, and one or more PCDs 12. The one or more PCDs 12 may be associated with one or more users 210 (e.g., clinicians) and/or patients 220. For purposes of this disclosure, a user 210 is a clinician or other authorized user of a PCD 12 or other medical device, and a patient 220 is an individual using or otherwise receiving medical treatment from a PCD 12 or other medical device. The server 30, one or more device terminals 32, and/or one or more PCDs 12

(generally referred to as "communicatively coupled devices") are communicatively coupled via the network 10. The communicatively coupled devices can share information using the network 10. For example, a PCD 12 can provide the server 30 and/or other PCDs 12 information corresponding to one or more of its associated users 210 and/or patients 220, location data, presented manifestations of notifications, and/or other manifestation of notification data (e.g., manifestations of notifications for nearby or adjacent patients 220 or PCDs 12, and/or manifestation configurations for users 210 patients 220, and/or PCDs 12).

In some implementations, the one or more users 210 are associated with one or more PCDs 12. For example, as shown in system 200, a first user 210-1 is associated with a first, second, third, and nth PCD 12-1, 12-2, 12-3, and **12-*n* (where n is an integer greater than zero); a second user 210-2 is associated with the first, fourth, and fifth PCD 12-1, 12-4, and 12-5; and nth user 210-*n* (where n is an integer greater than zero) is associated with the nth PCD 12-*n*. In some implementations, the one or more PCDs 12 are associated with the same patient (e.g., the first PCD 12-1 and the second PCD 12-2 are each associated with the first patient 220-1). Alternatively or additionally, in some implementations, the one or more PCDs 12 are associated with distinct patients (e.g., the third PCD-12-3 is associated with the second patient 220-2 and the fourth PCD 12-4 is associated with the third patient 220-3). Similarly, in some implementations, the one or more PCDs 12 are associated with the same or distinct users 210. For example, both the first user 210-1 and second user 210-2 are associated with the first PCD 12-1; however, the third PCD-12-3 is associated with the first user 210-1 and the fourth PCD 12-4 is associated with the second user 210-2**.

Figure 3:
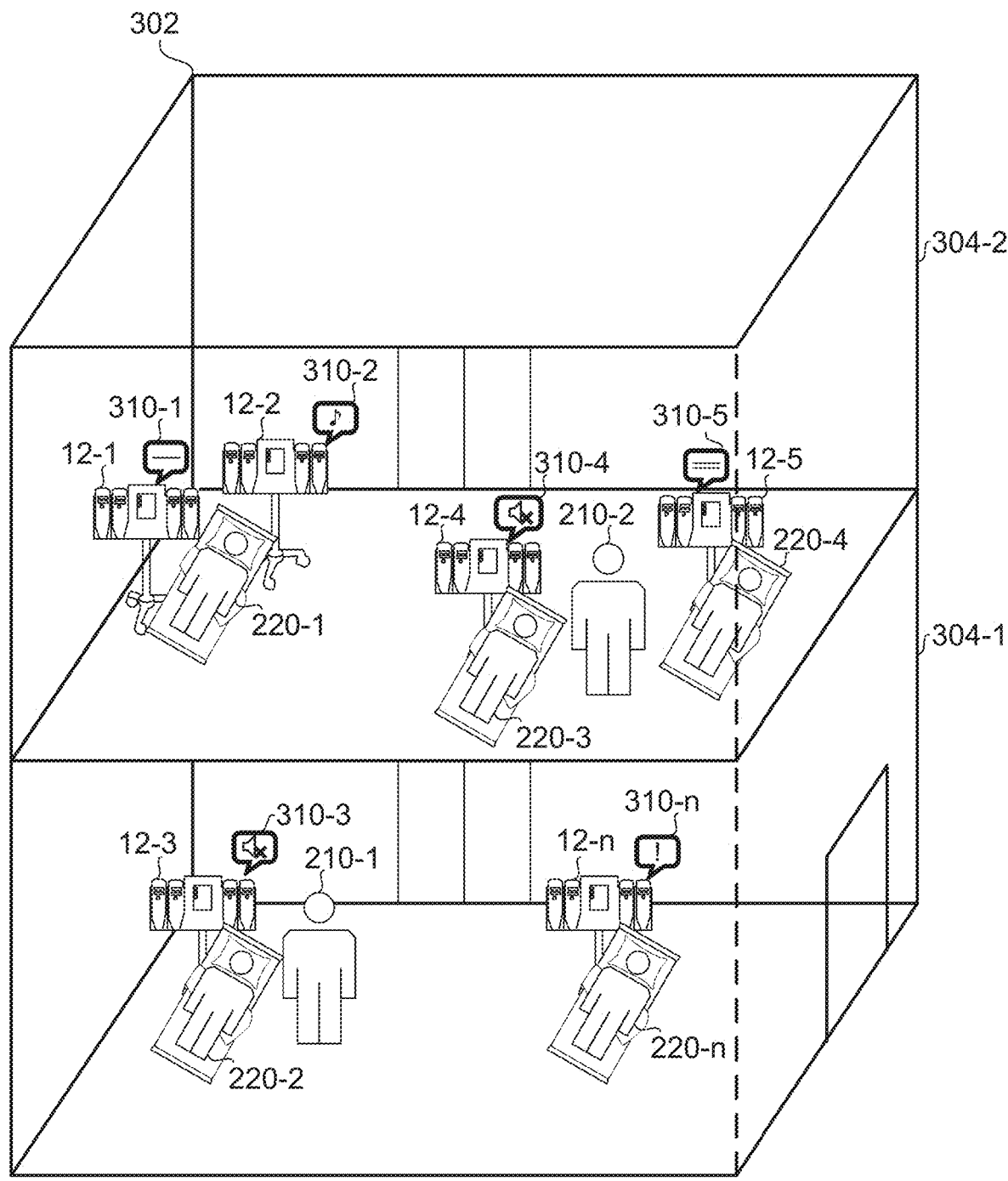
FIG. 3 illustrates adjustments to notifications of a point-of-care unit, according to various aspects of the subject technology.

FIG. 3 illustrates adjustments to manifestations of notifications of a PCD, according to various aspects of the subject technology. An operational overview 300 includes a building 302 with one or more floors (e.g., first floor 304-1 and second floor 304-2), one or more PCDs 12, one or more users 210, one or more patients 220, and/or one or more manifestations of notifications 310 of respective PCDs 12. As described above in FIG. 2, in some implementations, the users 210 and/or patients 220 are associated with the one or more PCDs 12. For simplicity, in operational overview 300, a first user 210-1, second user 210-2, and patients (220-1 through **220-*n*) are associated with the one or more PCDs (12-1 through 12-*n*) as described in FIG. 2. For example, the first user 210-1 is associated with the first, second, third, and nth PCD (12-1, 12-2, 12-3, and 12-*n*) and the second user 210-2 is associated with the first, fourth, and fifth PCD (12-1, 12-4, and 12-5**).

As illustrated in operational overview 300, the one or more PCDs 12 present one or more notifications 310 simultaneously. The one or more notifications 310 are associated with one or more human perceivable manifestations (e.g., visual, audio, and/or other human recognizable cues). More specifically, the PCDs 12 present several manifestations of notifications 310 at the same time and in the same general area (e.g., adjacent beds, same room, same floor, etc.). Each presented notification 310 includes one or more of an audio manifestation (e.g., sound represented by a musical chord), visual manifestation (e.g., text represented by a dash), and/or other human perceivable manifestations (e.g., haptic feedback and/or other recognizable cue; represented by an exclamation mark). For example, the first PCD 12-1 presents one or more manifestations of a first notification 310-1, the second PCD 12-2 presents one or more manifestations of a second notification 310-2, the third PCD 12-3 presents one or more manifestations of a third notification 310-3, the fourth PCD 12-4 presents one or more manifestations of a fourth notification 310-4, the fifth PCD 12-5 presents one or more manifestations of a fifth notification 310-5, and the nth PCD **12-*n* presents one or more manifestations of an nth notification 310-*n*. In some implementations, the presented notifications 310** include at least two of an audio manifestation, visual manifestation, and/or other human perceivable manifestation.

In some cases, a user 210 is occupied with a patient 220 or is away and cannot address a notification right away. Manifestations of notifications 310 that go unattended can create considerable stress and strain to the user 210 and others in the area (e.g., other users 210 and/or one or more patients 220). In some situations, loud and/or overt manifestations of notifications can disturb resting patients 220 (e.g., if presented in the middle of the night or early hours of the day). In some situations, a patient 210 may have an increased sensitivity to one manifestation of a notification 310 over another (e.g. increased light sensitivity, increased hearing sensitivity, or other conditions). Passive detection features of the PCD 12 ease the stress and strain due to such manifestations. In particular, the passive detection features of the PCD 12 include, the PCD 12 (or server 30), determining that the user 210 has authorized access to the PCD 12 to address the notification 310, or the PCD 12 (or server 30) detecting that the (authorized) user 210 is focused on the PCD 12. In some implementations, detecting that the user 210 is focused on the PCD 12 is performed after the user 210 is authorized and/or before the PCD 12 locks.

In some implementations, the passive detection features of the PCD 12 are based on user data (e.g., clinician data), patient data (e.g., patient information and/or patient specific configuration data), user interactions with the PCD 12, quantity of user interactions with the PCD 12 (e.g., number of touches, parameters programmed, etc.), user privileges and/or user ownership of a program of the PCD 12 (e.g., user 210 that programmed the PCD 12 and/or other users 210 that are authorized to operate one or more features of the PCD 12), and/or user privileges and/or user ownership of a program of a channel (e.g., functional model 16, 18, 20, 22; FIG. 1) of the PCD 12. For example, the PCD 12 can detect that the user 210 is focused on the PCD 12 based on a user 210 programming the PCD 12 or programming one or more functional models 16, 18, 20, 22 of the PCD 12 (e.g., programming a pump of the PCD 12), the number of inputs that the user 210 provides the PCD 12, the latest (e.g., most recent) input provided by the user 210 to the PCD 12, etc. In some implementations, the user privileges and/or user ownership of a program include specific configurations for a user 210 based on their role (e.g., junior clinician, senior clinician, support staff, etc.). For instance, a senior clinician may be provided more time than a junior clinician to address a notification, a senior clinician may be provided more time than a junior clinician before the PCD 12 requests for authentication and/or locks after being accessed, a senior clinician may be provided more time in-between inputs than a junior clinician before the PCD 12 requests for authentication and/or locks after being accessed, etc.

In order to access a PCD 12, a user 210 must be authorized to access (or operate) the PCD 12. In this way, the PCD 12 prevents its unauthorized use. A user 210 can access the PCD 12 in various ways, such as providing their login credentials (or other unique identifier (UID)) to a PCD 12 and/or using a proximity and/or vicinity cards, RFID, NFC, short range transmitters, providing a wireless message, and/or other methods known in the art. A user's request to access a PCD 12 includes a request to be authenticated by the PCD 12 and/or the server 30 (FIG. 1). As such, when the user 210 attempts to access a PCD 12, the PCD 12 is able to authenticate the user 210 with the user's 210 access request. In some implementations, the PCD 12 receives the user's access (and authentication) request when the user is in proximity to the PCD 12 (e.g., when the user 210 has a proximity card, short-range transmitter, etc.). Proximity, for purposes of this disclosure, means that the one user 210 is in the same room as the PCD, within five feet of the PCD, within three feet of the PCD, and/or making contact with the PCD 12 (e.g., making contact with a badge). In some implementations, the user 210 can access the PCD 12 using biometric authentication (e.g., using an iris scan, thumbprint, voice recognition, or similar).

When the PCD 12 receives the user's 210 access request, the PCD 12 and/or server 30 determine whether the user 210 is authorized to use the PCD 12. In some implementations, the PCD 12 and/or server 30 compare the user's login credentials against stored credentials (e.g., in database 56). Alternatively or additionally, in some implementations, the PCD 12 and/or server 30 decode signals received by proximity and/or vicinity cards, RFID, NFC, short range transmitters and compare the decoded signals with stored authenticated counterparts (e.g., in database 56). Additionally or alternatively, in some implementations, the PCD 12 and/or server 30 determine whether the user 210 is authorized based on the user's association with the PCD 12 and/or patient 220. For example, the first user 210-1 can provide an access request to the third PCD 12-3, and the PCD 12-3, upon determining that the first user 210-1 is authorized to access the third PCD 12-3, will grant access to the first user 210. In some implementations, if the PCD 12 determines that the user 210-1 is not authorized to operate the PCD 12, the PCD 12 will forgo granting access to the user 210. Additionally or alternatively, in some implementations, if the PCD 12 determines that the user 210-1 is not authorized to operate the PCD 12, the PCD 12 may lock itself and/or generate an additional notification.

The PCD 12 and/or server 30 adjusts at least one manifestation of a notification 310 for a predetermined period of time after authenticating and providing access to the PCD 12 to the user 210, or after detecting that the user 210 is focused on the PCD 12. The predetermined period is the duration of time that the at least one manifestation of the notification 310 is adjusted (e.g., suppressed, silenced, and/or otherwise changed as discussed below). In some implementations, the predetermined period of time (i.e., blackout period) is at least 30 seconds. In some implementations, the predetermined period of time is equal to the time that the PCD 12 is first accessed to the time that the PCD 12 logs the user 210 out and/or locks. In some implementation, the predetermined period of time is equal to the time that the PCD 12 is first accessed to the time that the PCD 12 (or server 30) no longer detects that the user 210 is focused on the PCD 12 (e.g., the user 210 is no longer providing inputs to the PCD 12 (or functional models 16, 18, 20, 22), has moved a predetermined distance from the PCD 12, has exceeded a time to address a notification (based on user privileges and/or user ownership), and/or other passive detection features described above). In some implementations, the predetermined period of time is based on a user's 210 role (e.g., senior or expert clinicians have a longer predetermined period of time than junior clinicians and support staff).

Alternatively or additionally, in some implementations, the PCD 12 and/or server 30 dynamically determines the predetermined period of time based on the PCDs 12 operation and/or any auxiliary medical device coupled to the PCD 12. For example, in some implementations, the PCD 12 includes (or operates as) an infusion pump, and dynamically determines the predetermined period of time based, in part, on a drug being infused, alarm type, user preference, user privileges and/or user ownership (e.g., role as described above), whether user is logged into the infusion pump, whether infusion pump is locked, and/or user proximity to the infusion pump. In another example, when the user 210 is 1 ft. away from a PCD 12 presenting a manifestation of a notification, the PCD 12 may determine a predetermined period of time that is longer (e.g., 5 min) because the user 510 is nearby to attend to the patient 220; however, if the user moves away from the PCD 12 (e.g., a different room, floor, etc.), the predetermined period of time is shortened (e.g., less than 30 sec). In some implementations, the one or more alarm types include general information useful to a user 210 and/or a type of fault detected by the PCD 12 and/or any auxiliary medical device coupled to the PCD 12. For example, an alarm type can indicate a flow error, occlusion (and its general location), that infusion has ended or is near ending, callback, and/or any other type of general information or detected fault that is relevant to the user 210. In some implementations, the PCD 12 is caused to receive a parameter to control delivery of a fluid (at the PCD 12 or other medical device) via the PCD 12, and a user interaction at the PCD 12 includes receiving the parameter.

In some implementations, adjusting at least one manifestation of the notification 310 includes silencing a notification (i.e., temporarily dismissing and/or muting a notification). In some implementations, adjusting at least one manifestation of the notification 310 includes changing a color, flash, font, banner, overlay, brightness, volume, tone, pitch, patterns, and/or rate of the at least one manifestation of the notification 310 such that it does not generate additional stress or strain. In some implementations, adjusting at least one manifestation of the notification 310 includes increasing or decreasing a degree or magnitude of the at least one manifestation of the notification 310 (e.g., increasing or decreasing the volume, brightness, pitch, rate, etc.).

In some implementations, adjustments to the one or more manifestations of the notifications 310 are based on user data, patient data, user interactions with the PCD 12, quantity of user interactions with the PCD 12, user privileges and/or user ownership of a program of the PCD 12, and/or user privileges and/or user ownership of a program of a channel of the PCD 12. Additionally or alternatively, in some implementations, adjustments to the manifestations of the notifications 310 are based on PCD 12 specific data for the manifestations of notifications (e.g., in database 56) and/or patient monitoring (e.g., tracking of patient condition and treatments over time). For example, a PCD 12 may present a manifestation of a notification 310 in the middle of the night, and the PCD 12, when accessed by a user 210, adjusts the presented manifestation of the notification 310 to avoid disturbing nearby patients 220. Alternatively, in some implementations, the presented manifestation of the notification 310 may be adjusted to avoid disturbing the patient 220 while remaining human perceivable (e.g., removing audible manifestation of the notification and/or changing the audible manifestation to a visible manifestations). Alternatively or additionally, in some implementations, adjustments to the one or more manifestations of the notifications 310 are based, at least in part, on detected environmental conditions within proximity of the PCD 12. The environmental conditions may include time, light level, noise level, temperature, number of functional modules 16, 28, 20, 22 (e.g., pumping modules) associated with the PCD 12, patient information, patient monitoring data, medical device location (e.g., care area), or the like. For example, consider the situation where two functional modules are attached to the PCD 12. While a first functional module is being programmed the other functional module may raise a notification. In this instance, a clinician's attention is already focused on the PCD 12 where the issue related to the notification is situated. Accordingly, the PCD 12 may apply an adjustment to the notification from the second module. The adjustment may be to silence or reduce the volume for an audio manifestation of the notification.

In one example, a first user 210-1 may have adjustments to audio manifestations disabled (e.g., auto silence may be disabled) based on the first user's 210-1 role (e.g., junior clinician or clinician support) and a second user 210-2 may have adjustments to audio manifestations enabled (e.g., auto silence may be enabled) based on the second user's 210-2 role (e.g., senior clinician). In another example, a first user that programmed the PCD 12 for a patient (e.g., programmed an infusion pump treat a patient) accesses the PCD 12, the auto silence may be activated; however, a second user that never programmed the patient's PCD 12 (or that did not program a channel presenting a manifestation of the notification 310) accesses the PCD 12, the auto silence may be disabled (i.e., the PCD would present all manifestations of the notification to the second user because the second user had no prior interaction with the specific PCD associated with the notification). In some implementations, PCD 12 data (e.g., programming history, access history, patient history, etc.; stored in a database 56 internal to the PCD 12, and/or the external database 37; FIG. 1) is analyzed to determine one or more adjustments to the one or more manifestations of the notifications 310.

Additionally or alternatively, in some implementations, adjustments to the manifestations of the notifications 310 are based on the user preferences. For example, a user 210 may configure the PCD 12 to use a particular color, font, background, sound, pitch, etc. In some implementations, adjustments to the manifestations of the notifications 310 are based on user 210 condition (e.g., user is color blind, deaf in one ear, sensitive to certain colors/sounds, etc.). In some implementations, the adjustments to the manifestations of the notification 310 apply to other human perceivable manifestations of the PCD 12. For example, while a PCD 12 adjusts manifestation of the notification 310, the PCD 12 may also adjusts keypresses, new notifications, and/or any other steps that create noise or are overtly perceivable (i.e., the PCD 12 may operate in a "silent mode" when accessed by a user 210 and/or when it is detected that the user 210 is focused on the PCD 12).

In some implementations, while a user 210 is accessing (or operating) a first PCD 12, a second PCD 12 that is associate with the user 210 presents one or more manifestations of a notification 310. In some implementations, the one or more manifestations of the notification presented by the second PCD 12 can be presented to the user 210 via the first PCD 12. If the second PCD 12 is in proximity to the first PCD 12, the user 210 can acknowledge and adjust one or more manifestations of the notification 310 presented by the second PCD 12 for a predetermined period of time. For example, as illustrated in operational view 300, the second user 210-2 is responding to one or more manifestations of the fourth notification 310-4 presented by the fourth PCD 12-4, and, while the second user 210-2 is focused on the fourth PCD 12-4, manifestations of the fifth notification 310-5 are presented (or are about to be presented) by the fifth PCD 12-5. When the second user 210-2 first accesses the fourth PCD 12-4, at least one manifestation of the fourth notification 310-4 is adjusted (e.g., silenced). Because the second user 210-2 is also associated with the fifth PCD 12-5 and in proximity to the fifth PCD 12-5, the one or more manifestations of the fifth notification 310-5 presented by the fifth PCD 12-5 may be acknowledged by the second user 210-2 at the fourth PCD-4 (and adjusted). More specifically, one or more manifestations of notifications 310 presented by other PCDs 12, while a user 210 is accessing a particular PCD 12, are not automatically adjusted when the user 210 first accesses or while accessing the particular PCD 12. The user 210 has to be in proximity to the other PCDs 12 and has to acknowledge the notification before being able to adjust one or more manifestations of the notifications presented by the other PCD 12. Additionally or alternatively, the one or more manifestations of notifications 310 are adjust based on a user's 210 location and the PCD 12 they are focused on (to prioritize notifications by location, improve user interaction, reduced strain, etc.).

Figure 4:
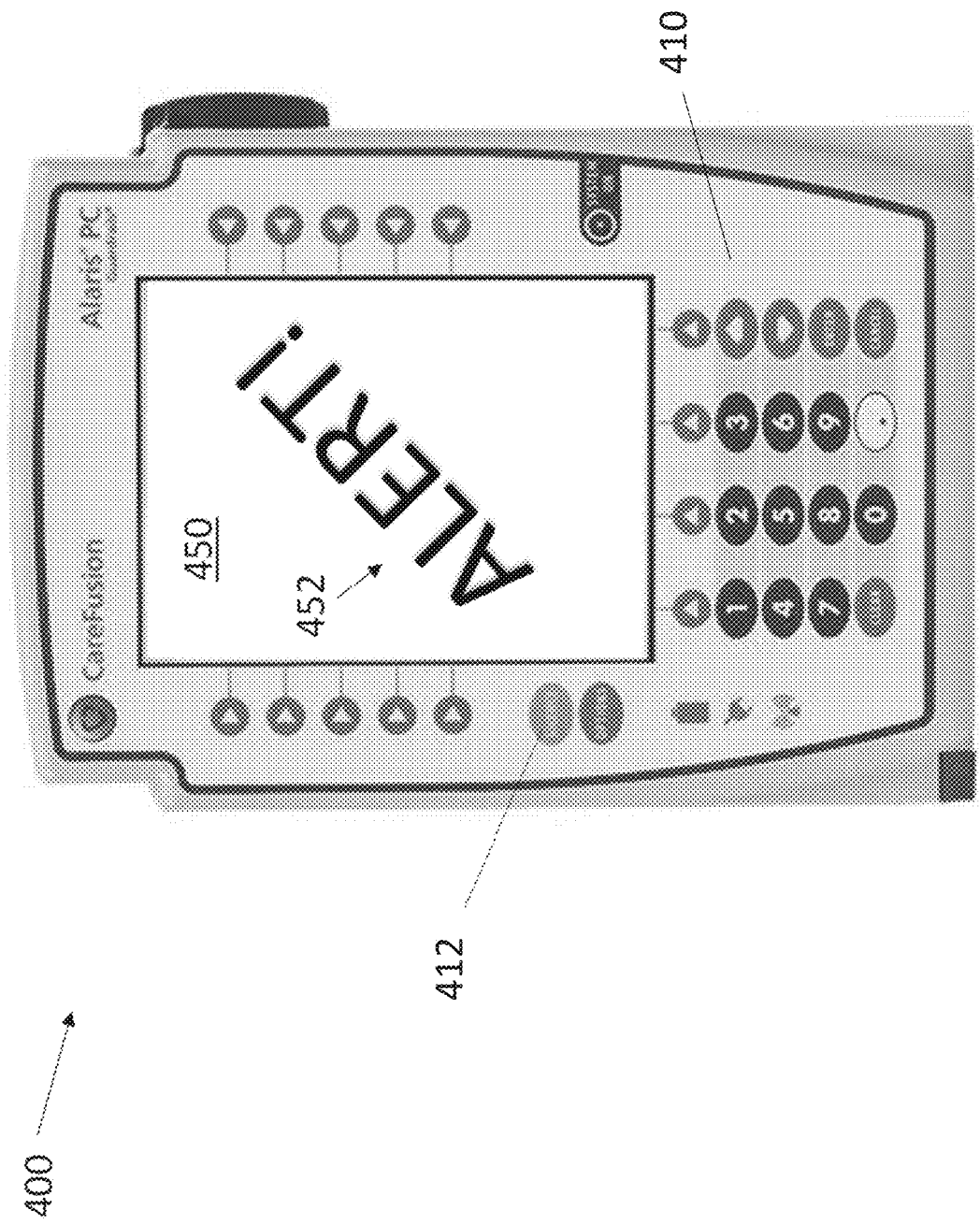
FIG. 4 illustrates a patient care device interface with a dedicated silence button, according to various aspects of the subject technology.

FIG. 4 illustrates a PCD interface with a dedicated silence button, in accordance with some implementations. The PCD interface 400 includes one or more input devices 410 and one or more output devices 450. The input devices 410 enable a user 210 to communicate information and select commands to the PCD 12. The input devices 410 include one or more alphanumeric buttons and/or command buttons (e.g., "clear," "enter," "cancel," etc.). In some implementations, the input devices 410 include a silence button 412 (also referred to as a silent notification feature) that can be deliberately activated (e.g., with express intent by a user 210) to adjust the notification manifestations. The silence button 412 when activated adjusts a manifestation of the notification generated and presented by the PCD 12 (i.e., suppresses, silences, or changes one or more manifestations of the notification as described above in reference to FIG. 3).

In some instances, an unauthorized user (such as a family member or other visitor of the patient) may activate the silence control element (i.e., the silence button 412). While well intentioned, silencing notifications can delay identification of a safety issue to a clinician caring for the patient. To overcome this limitation, the notification manifestations are adjusted after the user 210 accesses the PCD 12 and/or after the PCD 12 detects that the user 210 is focused on the PCD 12. As described above in reference to FIG. 3, the user 210 can access the PCD 12 by providing authentication information or otherwise being an authorized user of the PCD 12. Alternatively or additionally, in some implementations, the PCD 12 can detect that the user 210 is focused on the PCD 12 based on user interaction with the PCD 12 and/or the number of user interactions with the PCD 12. In some implementations, the silence button 412 is disabled such that it is not activated accidentally or by unauthorized user. In some implementations, disabling the silence button 412 includes suppressing signals received from an electromechanical input of the PCD 12 (i.e., suppressing a signal of the silence button 412 when pressed). Upon authentication of the user 210, the silence button 412 may be enabled. The silence button 412 may be enabled for a predetermined period of time or until the PCD 12 detects that the user 210 is no longer focused on the PCD 12 such as by detecting a log-off or no longer detecting a user authentication device (e.g., RFID) within the proximity of the PCD 12.

The one or more output devices 450 include a display. In some implementations, the one or more output devices 450 include one or more speakers, illuminating devices (e.g., LEDs, strobe lights, etc.), one or more haptic devices, etc.

The PCD 12 utilizes the one or more output devices 450 to present to the user 210 the human perceivable manifestations of notifications. For example, a manifestation of a notification 452 ("ALERT!"). Although not shown, the manifestation of a notification 452 can include additional audio and/or visual notifications. One or more of the manifestations of a notification 452 can be suppressed for a predetermined period of time such as to ease or eliminate the stress and strain on patients 220 and users 210, as described herein. For example, the manifestation of the notification 452 can include a flashing light and a ringing alarm in addition to the ALERT! message. Adjustments to the manifestation of the notification 452 can suppress one or more of the ringing alarm, flashing light, and the ALERT! message in order to ease or eliminate the stress and strain on patients 220 and users 210. As described above, manifestations of a notification that includes an audio, visual, and/or other human perceivable cues can be adjusted for a predetermined period of time to ease the stress and strain. More specifically, an audio or video manifestation of the notification can be suppressed for the predetermined period of time. In this way, the patient 220 and/or the user 210 are not continuously subjected to the manifestation of the notification.

Figure 5B:
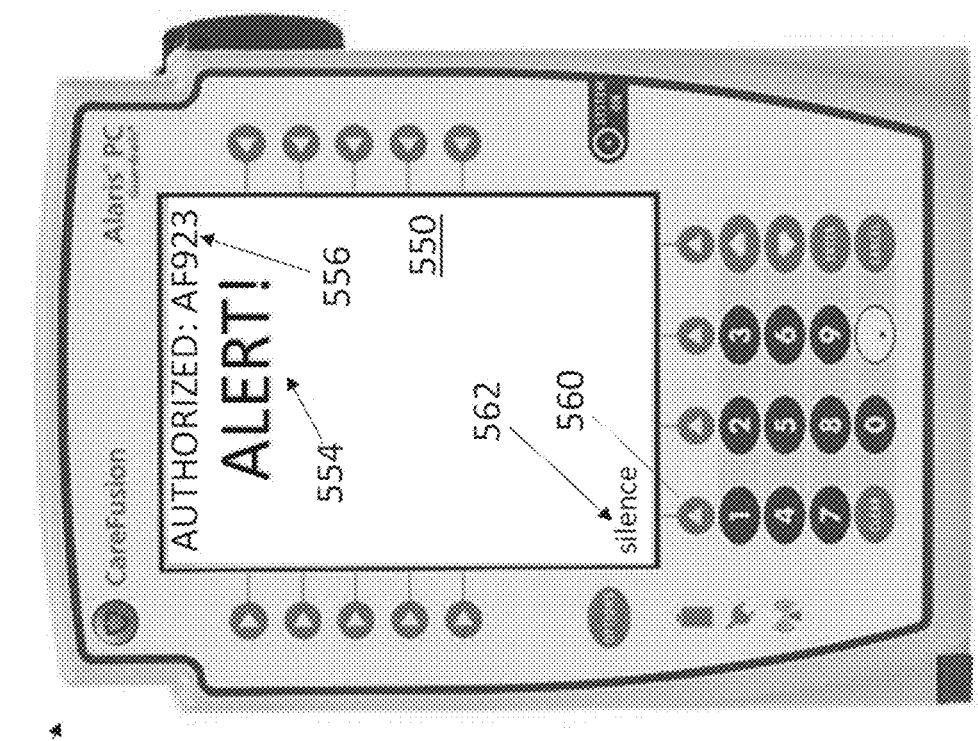
FIGS. 5A and 5B illustrate a patient care device interface without a dedicated silence button, according to various aspects of the subject technology.
Figure 5A:
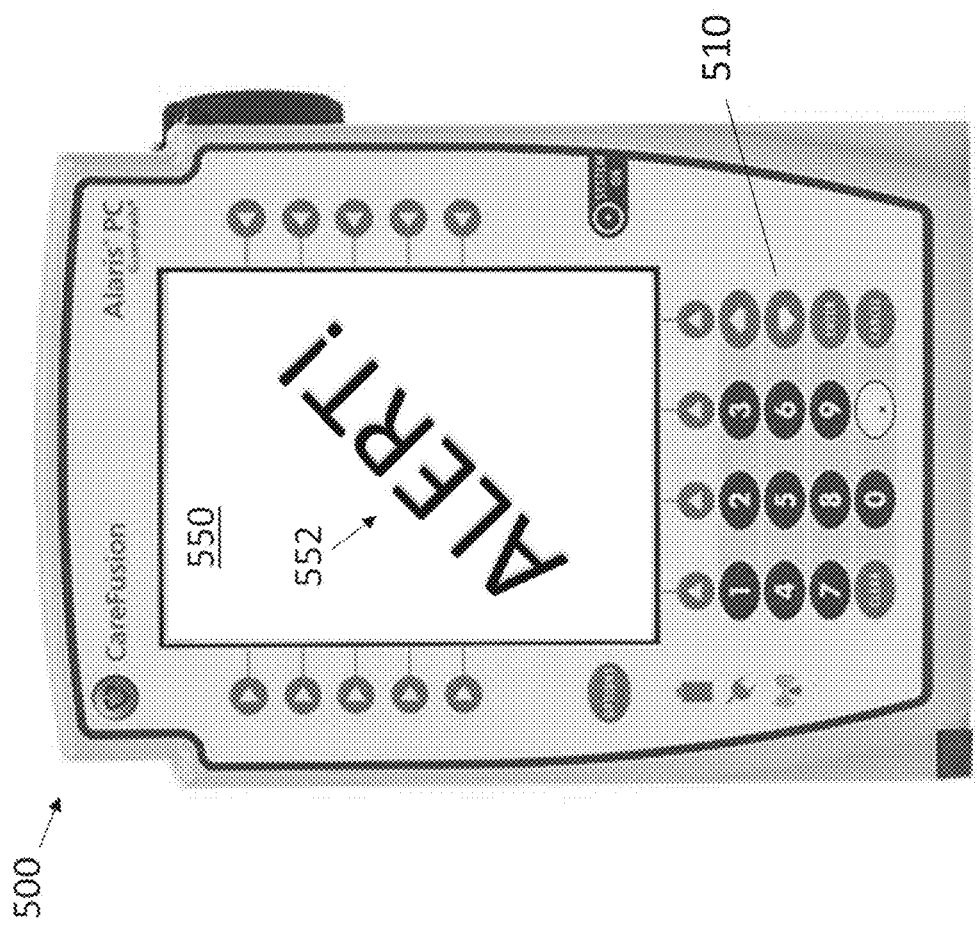

FIGS. 5A and 5B illustrate a PCD interface without a dedicated silence button, in accordance with some implementations. The PCD interface 500 includes one or more input devices 510 and one or more output devices 550. The input devices 510 enable a user 210 to communicate information and select commands to the PCD 12. The input devices 510 include one or more alphanumeric buttons and/or command buttons (e.g., "clear," "enter," "cancel," etc.). To avoid accidental or unauthorized activation of the PCD 12's silence control element, a dedicated silence button is removed from the PCD 12. In some implementations, the dedicated silence button is a hidden a control element and displayed after user authentication as described below. The user 210 can access the PCD 12, and/or the PCD 12 can detect that the user 210 is focused on the PCD 12 as described above in reference to FIGS. 3 and 4. In some implementations, the PCD 12 activates a control element for acknowledging the notification based at least in part on a detection that the user is focused on the PCD 12 (or accessing the PCD 12). In some implementations, upon activation of the control element, the PCD 12 adjusts the presentation of the at least one of the human perceivable manifestations of the notification. Similar to FIG. 4, the one or more output devices 550 include a display. In some implementations, the one or more output devices 550 include one or more speakers, illuminating devices (e.g., LEDs, strobe lights, etc.), one or more haptic devices, etc. The PCD 12 utilizes the one or more output devices 550 to present to the user 210 the human perceivable manifestations of notifications (e.g., manifestations of a notification 552 "ALERT!").

FIG. 5B illustrates the PCD interface without a dedicated silence button after it has been accessed by a user, in accordance with some implementations. In some implementations, the one or more output devices 550 of the PCD interface 500 present to the user 210 an adjusted manifestation of the notification 554, user indicator 556, and one or more on screen labels 562 (e.g., "silence" label). In some implementations, the adjusted manifestation of the notification 554 includes a repositioning, resizing, and/or recoloring of the initial manifestations of the notifications 552. Other adjustments (described herein) can be applied to the manifestations of the notification 552 to ease or eliminate the stress and strain on the user 210 and/or patient 220. The user indicator 556 identifies the user 210 that accessed and/or is currently focused on the PCD 12. The one or more on screen labels 562 are associated with one or more input devices 510. For example, silence label is associated with a command button 560 that when pressed adjusts the manifestation of the notification 552 (to adjusted manifestation of the notification 554). In some implementations, the one or more on screen labels 562 are presented to the user 210 after the user 210 has accessed the PCD 12 or while the PCD 12 detects that the user 210 is focused on the PCD 12.

Figure 6B:
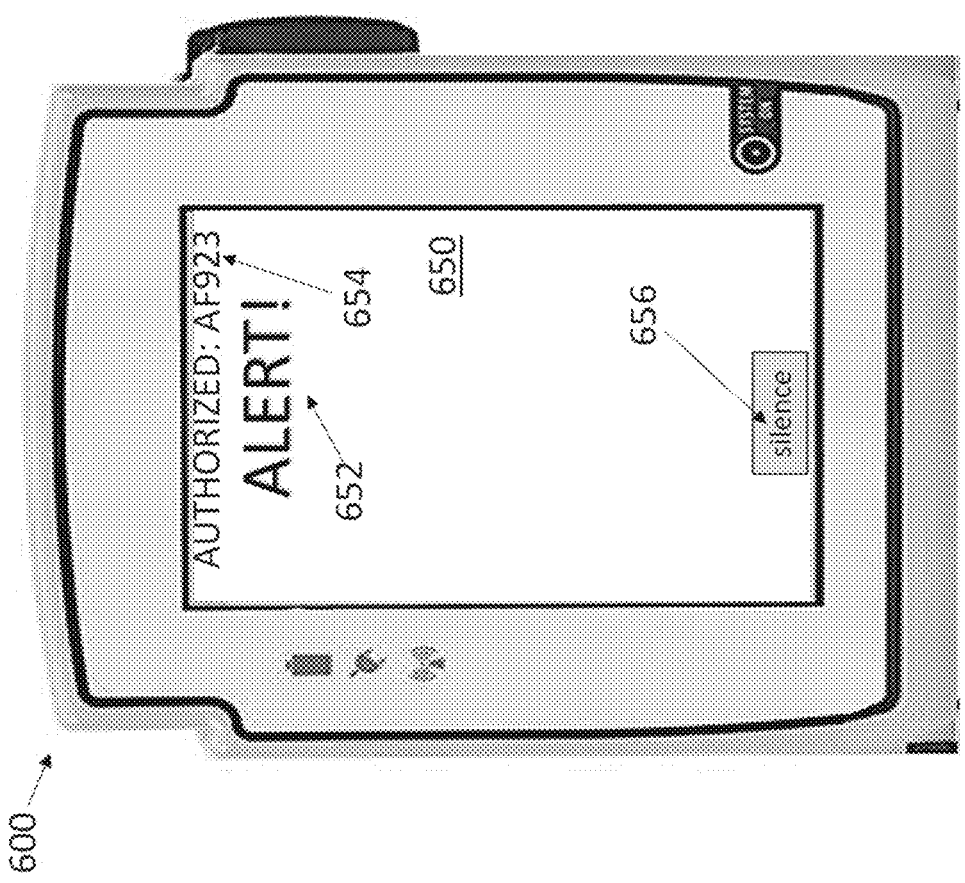
FIGS. 6A and 6B illustrate a patient care device interface with a touch screen display, according to various aspects of the subject technology.
Figure 6A:
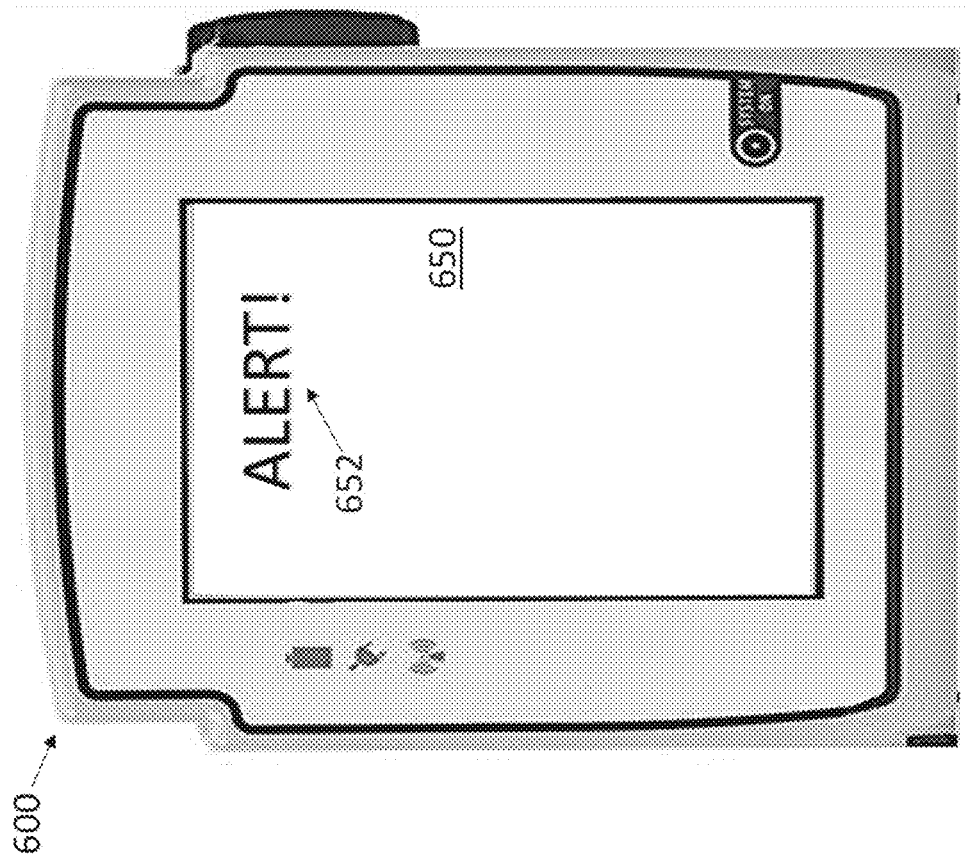

FIGS. 6A and 6B illustrate a PCD interface with a touch screen display, in accordance with some implementations. The PCD interface 600 includes one or more input/output devices 650. The input/output devices 650 enable a user 210 to provide information to and/or receive information from the PCD 12 as well as select one or more commands. In some implementations, the input/output devices 650 include a touch screen display. Similar to FIGS. 5A and 5B, a dedicated silence button is removed from the PCD 12 to avoid accidental or unauthorized activation of the PCD 12's silence control element. The user 210 can access the PCD 12, and/or the PCD 12 can detect that the user 210 is focused on the PCD 12 as described above in reference to FIGS. 3 and 4. Additionally, in some implementations, the one or more input/output devices 650 include one or more speakers, illuminating devices (e.g., LEDs, strobe lights, etc.), one or more haptic devices, etc. The PCD 12 utilizes the one or more input/output devices 650 to present to the user 210 the human perceivable manifestations of notifications (e.g., manifestations of a notification 652 "ALERT!").

FIG. 6B illustrates the PCD interface with a touch screen display after it has been accessed by a user, in accordance with some implementations. In some implementations, the one or more input/output devices 650 of the PCD interface 600 present to the user 210 the manifestation of the notification 652, user indicator 654, and one or more on screen UI control elements 656 (e.g., "silence" UI control element). The user indicator 654 identifies the user 210 that accessed and/or is currently focused on the PCD 12. The one or more on screen UI control elements 656 can be activated to activated (e.g., with express intent by a user 210) to initiate one or more commands of the PCD 12. For example, an on-screen UI control element 656 labeled "silence" adjusts the manifestation of the notification 652 (to adjusted manifestation of the notification 554). In some implementations, the one or more on screen UI control elements 656 are presented to the user 210 after the user 210 has accessed the PCD 12 or while the PCD 12 detects that the user 210 is focused on the PCD 12. In some implementations, the PCD 12 activates a control element of the medical device for acknowledging the notification based at least in part on said detecting. In some implementations, upon activation of the control element, the PCD adjusts the presentation of the at least one of the human perceivable manifestations of the notification.

As shown in FIGS. 4-6B, in some implementations, a medical device (e.g., PCD 12; FIGS. 1-3) for reducing generated alarm strain includes a display to present visually perceivable information, an audio output to present audibly perceivable information, one or more processors coupled with the display and the audio output and memory storing one or more instructions that, when executed by the one or more processors, cause the medical device to perform operations. The one or more instructions, when executed by the one or more processors, cause the medical device to receive a notification regarding the medical device. The notification is associated with an audible manifestation and a visual manifestation. The one or more instructions, when executed by the one or more processors, further cause the medical device to detect that a user is focused on the medical device. Detecting that the user is focused on the medical device is based on authenticating the user to the medical device or detecting user interaction via the medical device. The one or more instructions, when executed by the one or more processors, further cause the medical device to, after said detection of the user, determine a volume adjustment to the audio output for presenting the audible manifestation and adjust the audio output to cause presentation of the audible manifestations according to the volume adjustment. In some implementations, the audio output presents the audible manifestation with the volume adjustment at a lower volume than the audio output would present the audible manifestation without the volume adjustment.

Figure 7:
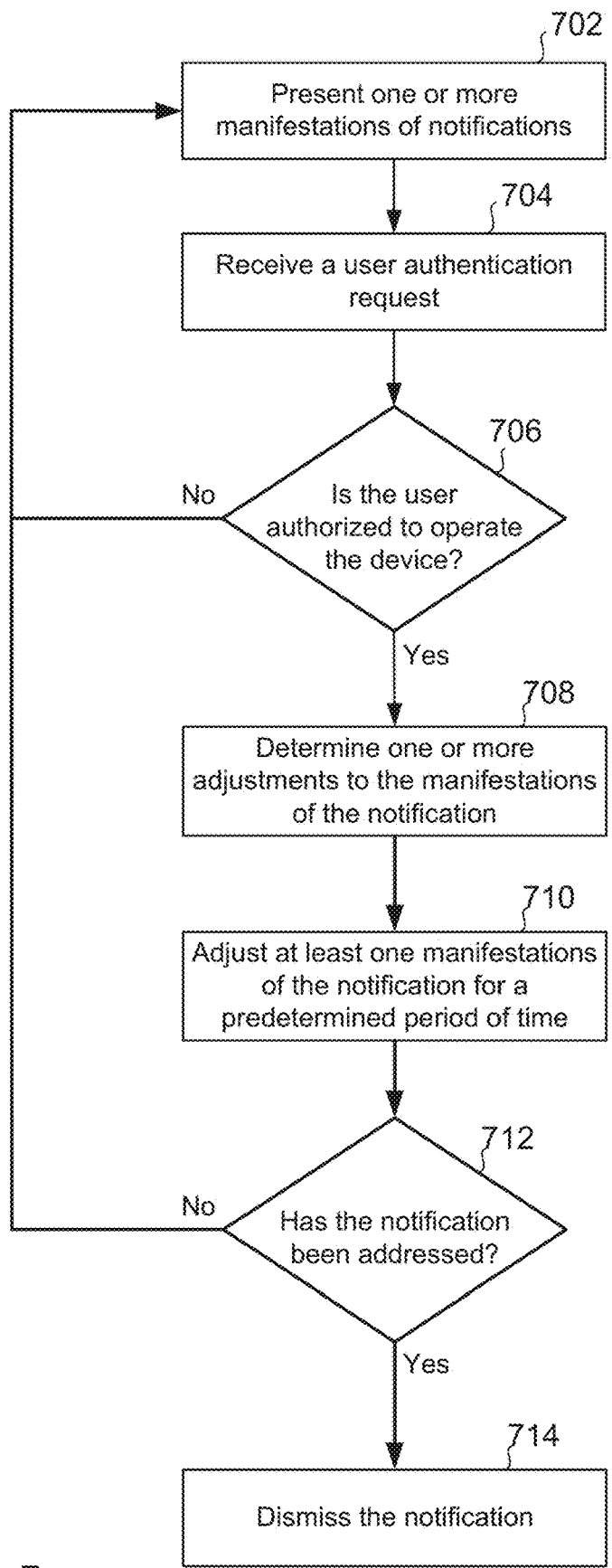
FIG. 7 illustrates a process for adjusting at least one manifestations of a notification presented by a patient care device, according to various aspects of the subject technology.

FIG. 7 illustrates different operations performed by a PCD and/or server, in accordance with some implementations. At least some of the operations are performed by a computer having a processor executing commands stored in a memory of the computer (e.g., CPU 50, and database 56; FIG. 1). In some implementations, information is transmitted between one or more devices in a system (e.g., server 30 and PCD 12; FIG. 1), such as sensor data, stored data, and/or user input information. The operations of the PCD 12 and/or server 30 consistent with the present disclosure may include at least some, but not all, of the operations illustrated in FIG. 7, performed in a different sequence. Similarly, one or more operations illustrated in FIG. 7 may be optional. Furthermore, the operations of the PCD 12 and/or server 30 consistent with the present disclosure may include at least two or more steps as in FIG. 7 performed overlapping in time, or almost simultaneously. For brevity, the examples provided below are performed at a PCD 12.

FIG. 7 illustrates a process for adjusting at least one manifestations of a notification presented by a PCD, in accordance with some implementations. In some implementations, a PCD 12 presents 702 one or more manifestations of a notification 310 (FIG. 3). For example, a PCD 12 associated with a patient 220 (FIG. 2) can present a manifestation of a notification 310 to alert a user 210 (FIG. 2) that the patient 220 needs some assistance.

While the PCD 12 is presenting the one or more manifestations of the notification, the PCD 12 receives 704 a user authentication request from the user 210. In some implementations, the authentication request is received with a request to access the PCD 12. As mentioned above, the user 210 can provide the access and/or authentication request using login credentials, a proximity and/or vicinity cards, RFID, NFC, short-range transmitters, and/or other methods known in the art. For example, while the PCD 12 is presenting the manifestations the notification, the user 210 can use their personal badge (i.e., a proximity card) to make contact (e.g., touch) with the PCD 12. Alternatively or additionally, in some implementations, the PCD 12 can detect that an user 12 is focused on the PCD 12 based on one or more user inputs to the PCD 12 (or one or more of its functional models 16, 18, 20, 22; FIG. 1).

The PCD 12 determines 706 whether the user 210 (requesting access) is authorized to access the PCD 12. In some implementations, the PCD 12 determines that the user 210 is authorized to access the PCD 12 by comparing the received authentication information (e.g., credential, encoded signals, and/or encrypted signals) with stored authentication information (e.g., in database 56). For example, when the PCD 12 makes contact with the user 210's personal badge, the PCD 12 may receive encoded signals (including a user 210's authentication information). The PCD 12 may decode the encoded signal (or decrypt an encrypted signal) and compare the user's authentication information with stored authentication information. Additionally or alternatively, in some implementations, the PCD 12 determines whether the user 210 is authorized to access the PCD 12 by determining whether the user 210 is associated with the PCD 12 and/or the patient 220. In this way, user's 210 that are not assigned to a patient 220 and/or the PCD 12, cannot access the PCD 12. In some implementations, when the PCD 12 detects that the user 12 is focused on the PCD 12, the PCD determines whether the user 12 is authorized based on the user's 210 initial access request or by re-querying the user 210 (e.g., by requesting user authentication information or by receiving authentication information when the user 210 is in proximity (via a short-range transmitter)).

If the user's 210 authentication information does not match stored authentication information (and/or the user 210 is not associated with the PCD 12 and/or the patient 220), then the PCD 12 returns to operation 702 and continues to present one or more manifestations of the notification. In some implementations, the PCD 12 presents an additional manifestation of the notification indicating that an unauthorized attempt to access the PCD 12 was made. Additionally or alternatively, in some implementations, the PCD 12 may lock itself after the authentication request fails (i.e., no matching authentication information). By locking itself up, the PCD 12 prevents others from tampering with it.

If the user's 210 authentication information does match stored authentication information (and/or the user 210 is associated with the PCD 12 and/or the patient 220), then the PCD 12 determines 708 one or more adjustments to the manifestations of the notification. For example, PCD 12 may determine a type of adjustment (e.g., visual, audio, or other), the length of the adjustment (e.g., predetermined period of time), the degree of the adjustment (e.g., color change, brightness increase or decrease, volume increase or decrease, audio frequency increase or decrease, flash frequency increase or decrease, etc.). For example, a default manifestation for a notification can be a visual manifestation with an initial lumen configuration (e.g., light output). The PCD 12 may determine a subsequent lumen adjustment for the visual manifestation of the notification (e.g., decrease or increase in light output).

In some implementations, the determined adjustments to the manifestations of the notification are based on clinician data (e.g., in database 56). For example, a user 210 can have specific preferences for adjustments to the manifestations of the notification, such as preferred visual adjustments (changes in colors, backgrounds, flashes, etc.), preferred audio adjustments (frequencies, volume, pitches, etc.), physical accommodations (e.g., avoiding certain colors if the user 210 is color blind, ringing an alarm in a certain position if the clinician is deaf in one ear, avoiding bright colors or loud sounds if the user 210 is sensitive, etc.).

In some implementations, the adjustments to the manifestation of the notification are based on patient data (e.g., patient information such as age, sex, medical conditions, illnesses, diseases, etc.). The patient data includes patient specific configuration data (e.g., in database 56). In particular, a patient 220 can be associated with specific configurations for adjustments to the manifestations of the notifications, such as visual adjustments, audio adjustments, and/or other adjustments to the manifestations of notifications. The patient specific configurations for adjustments to the manifestations of the notifications allow the user 210 to easily identify the patient 210 and/or accommodate the patient's 220 health conditions. For example, a patient 220 with severely sensitive hearing can have patient specific configuration data that limits and/or removes audio manifestations of the notification, and adjustments to the manifestations of the notification avoid audio adjustments to the manifestations of the notifications that would worsen the patient's 220 condition.

In some implementations, the adjustments to the manifestations of the notification are based on PCD 12 specific data for the manifestations of notifications (e.g., in database 56). The PCD 12 specific data includes manifestations of the notifications that the PCD 12 is capable of presenting. For example, the PCD 12 specific data can indicate that the PCD 12 does not have any illuminating devices and therefore cannot present flashes or strobing manifestations of the notification. The clinician data, patient specific configuration data, and/or PCD 12 specific data is described above in reference to FIG. 1.

The one or more adjustments to the manifestation of the notification are applied for a predetermined period of time such as 30 sec, 1 min, 5 min, etc. In some implementations, the predetermined period of time is dynamically determined (as described above in reference to FIG. 3). By adjusting at least one manifestation of the notification for a predetermined period of time, the user 210 is able to ease or eliminate the additional stress and strain generated by ongoing manifestations of the notification until he or she can address the notification.

The PCD 12 adjusts 710 at least one manifestation of the notification for a predetermined period of time. In some implementations, the PCD 12 applies the adjustment to the manifestation of the notification automatically (as soon as the user has been authenticated). Alternatively, in some implementations, the PCD 12 determines the difference between the default manifestation and the adjusted manifestation, and if the difference is above a predetermined threshold, then the PCD 12 applies the adjustment to the manifestation of the notification. Alternatively, if the difference is above a predetermined threshold, then the PCD 12 forgoes applying the adjustment to the manifestation of the notification. For example, if the default volume level for an audio manifestation is 50 dB and the determined adjustment value results in an audio manifestation of 30 dB (a 40% decrease over the default), the PCD 12 will adjust the manifestation of the notification based on the determined adjustment value if the difference between the default and adjusted manifestation is above a predetermined threshold (e.g., 10% difference). The predetermined threshold can be defined by the user 210, an administrator of the clinic or hospital, or other entity that manages the hospital or clinic. For example, the predetermined threshold can be a difference of 5%, 10%, 20%, etc.

Adjusting the manifestation of the notification includes suppressing, silencing, and/or snoozing the manifestation of the notification. Alternatively or additionally, adjusting the manifestation of the notification includes making the manifestation of the notification less obtrusive such that it does not generate unwanted stress and strain (e.g., lowering the volume, lowering the brightness, removing a flash, selecting different colors, etc.). In some implementations, adjusting the manifestations of the notification includes making one manifestation prominent and making another manifestation less obvious. For example, a user 210 may be deaf and the PCD 12 may adjust audio manifestations of the notification to suppress sound and/or change the audio manifestations to visual manifestations. Additionally, the one or more adjustments to the manifestation of the notifications are described above in reference to FIG. 3. The degree or specific adjustments may be further determined using information about the clinician's attention. For example, the system may include adjustments to apply when the source of the notification is attended (e.g., "alerting during clinician interaction" or "attended alerting") and alternate adjustments to apply when the source of the notification is unattended (e.g., alerting when a clinician is not interacting with the module or associated PCD or "unattended alerting").

After waiting the predetermined period of time, the PCD 12 determines 712 whether the notification has been addressed. If the PCD 12 determines that the notification has not been addressed, then the PCD 12 returns to operation 702 and continues to generate the notification. For example, the user 210 can be treating a patient 220 that is associated with two PCDs 12 that are each generating notifications. In this example, the first PCD 12 generates a first notification and a second PCD 12 generates a second notification more urgent than the first notification. The user 210 may access the first PCD 12 associated with the patient and adjust, at least partially, the first notification (for a predetermined period of time) before turning to the second PCD 12 to attend to the second notification, which is more urgent. If the predetermined period of time for the first notification expires while the user 210 is operating the second PCD 12, the first PCD 12 will generate the first notification again.

In some implementations, if the user 210 is still operating the PCD 12 when the predetermined period of time expires, the user is prompted to acknowledge the notification. For example, the user 210 may respond to a notification generated by the PCD 12; however, the time needed to resolve the notification may be longer than the predetermined period of time. In such cases, the user 210 may be prompted to acknowledge the notification after the predetermined period of time has expired. In another example, the PCD 12 may generate a first and second notification that are both adjusted, at least partially, when the user accesses the PCD 12. Both the first and second notifications are adjusted for respective predetermined periods of time. If the predetermined period of time for the first and/or second notification expiries, the user 210 may be prompted to acknowledge the first and/or second notification. The first and second notifications can be generated at either the same time or any time before and/or after the user 210 is accessing the PCD 12. If the second notification is generated while the user 210 is accessing the PCD 12, the user 210 may be prompted to acknowledge the second notification. In some implementations, acknowledging the notification allows the user 210 to adjust, at least partially, the notification for another predetermined period of time or dismiss the notification if they are currently attending to it. If the PCD 12 determines that the notification has been addressed, then the PCD 12 dismisses 714 the notification and ends the process.

Figure 8A:
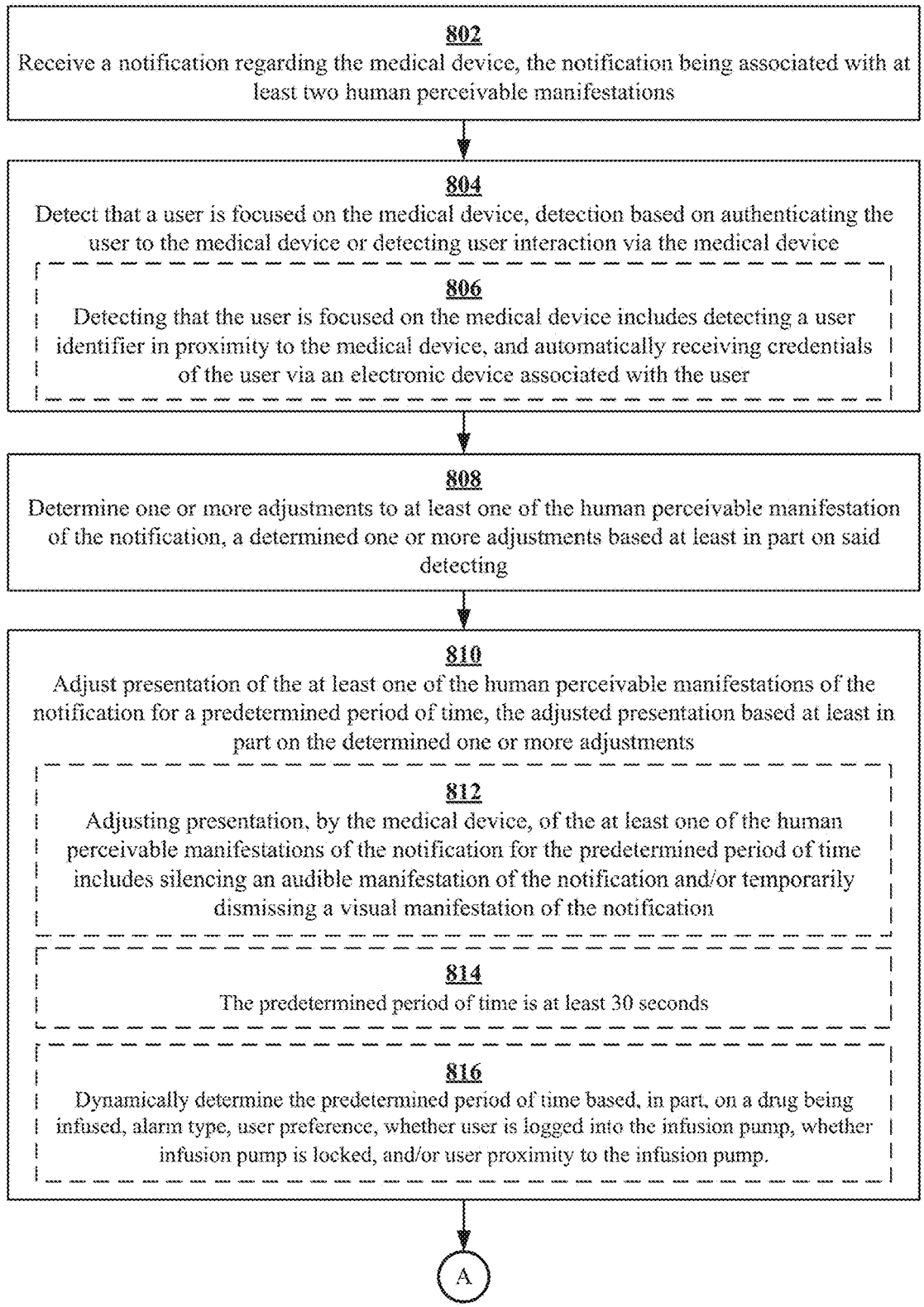
FIGS. 8A and 8B are flowcharts illustrating a method for adjusting at least partially one or more notifications generated by a point-of-care unit, according to various aspects of the subject technology.
Figure 8B:
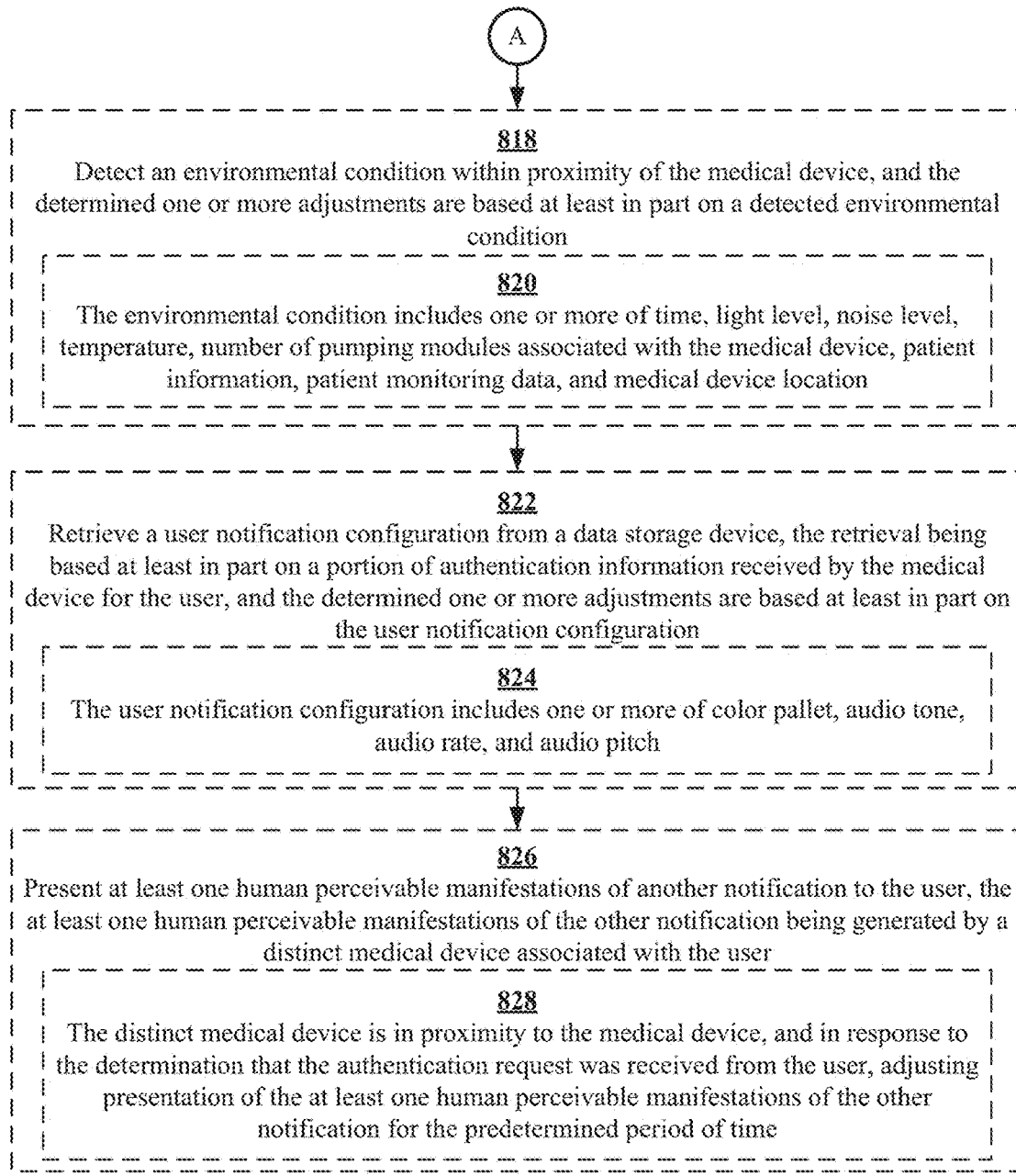

FIGS. 8A and 8B is a flowchart illustrating a method 800 for reducing alarm strain generated by a network of PCDs according to some implementations. Method 800 may be performed at one or more device terminals, PCD 12, and/or server 30. More specifically, the operations of the method 800 are performed by a computer having a processor executing commands stored in a memory of the computer (e.g., CPU 80, and database 56). In some implementations, information is transmitted between one or more devices in a system (e.g., server 30 and PCDs 12), such as patient information, user information, notification information, and/ or user input information. The operations of the method 800 consistent with the present disclosure may include at least some, but not all, of the operations illustrated in FIG. 8, performed in a different sequence. Similarly, one or more operations illustrated in FIG. 8 may be optional. Furthermore, the operations of the method 800 consistent with the present disclosure may include at least two or more steps performed overlapping in time, or almost simultaneously.

Method 800 includes receiving (802) a notification regarding the medical device (e.g., the PCD 12; FIG. 1), the notification being associated with at least two human perceivable manifestations. In some implementations, the at least two human perceivable manifestations include an audible and/or visible manifestation. In some implementations, the at least two human perceivable manifestations of the notification are not adjusted (e.g., silenced or dismissed) until a user 210 is detected to be focused on the medical device.

The method 800 further includes detecting (804) that a user is focused on the medical device. The user is detected to be focused on the medical device based on authenticating the user to the medical device or detecting user interaction via the medical device. In particular, the method 800 includes performing passive detection features described above in reference to FIG. 3. For example, a user 210 can provide an authentication request to access the medical device by inputting their login credentials (or other unique identifier (UID)) and/or using a proximity and/or vicinity cards, RFID, NFC, short range transmitters, and/or other methods known in the art, and the medical device (or server) determines whether the user 210 requesting to access the medical device is authorized to use the medical device. In some implementations, detecting (806) that the user is focused on the medical device includes detecting a user identifier in proximity to the medical device, and automatically receiving credentials of the user via an electronic device associated with the user (e.g., a short-range transmitter). In some implementations, detecting that the user is focused on the medical device includes detecting a badge associated with the user making contact with a medical device, the user being within 1 ft. of the medical device (e.g., 1 ft. radius), or other examples provided above in FIG. 3.

The method 800 includes determining (808) one or more adjustments to at least one of the human perceivable manifestation of the notification. A determined one or more adjustments are based at least in part on said detecting. For example, the determined one or more adjustments may be at least in part on user data (e.g., clinician data in a database 56 internal to the PCD 12, and/or the external database 37). The method 800 further includes adjusting (810) presentation of the at least one of the human perceivable manifestations of the notification for a predetermined period of time. The adjusted presentation based at least in part on the determined one or more adjustments. In some implementations, adjusting (812) presentation, by the medical device, of the at least one of the human perceivable manifestations of the notification for the predetermined period of time includes silencing an audible manifestation of the notification and/or temporarily dismissing a visual manifestation of the notification. In some implementations, the predetermined period of time is (814) at least 30 seconds. In some implementations, the method 800 includes dynamically determining (816) the predetermined period of time based, in part, on a drug being infused, alarm type, user preference, whether user is logged into the infusion pump, whether infusion pump is locked, and/or user proximity to the infusion pump. For example, a first drug may have side effects that require more attention than side effects of a second drug, and the method includes dynamically adjusting a first notification associated with the first drug to have a shorter predetermined period of time than a second notification associated with the second drug.

In some implementations, the method 800 includes detecting (818) an environmental condition within proximity of the medical device. The determined one or more adjustments are based at least in part on a detected environmental condition. In other words, the medical device can use one or more detected environmental conditions to adjust one or more manifestations of notifications. In some implementations, the environmental conditions include (820) one or more of time, light level, noise level, temperature, number of pumping modules associated with the medical device, patient information, patient monitoring data, and medical device location. In some implementations, the method 800 includes retrieving (822) a user notification configuration from a data storage device (e.g., clinician data in the database 56 internal to the PCD 12, and/or the external database 37). The retrieval is based at least in part on a portion of authentication information received by the medical device for the user 210. The determined one or more adjustments are based at least in part on the user notification configuration. In other words, the medical device can use clinician data to adjust one or more manifestations of notifications in accordance with the clinician's preferences, role (e.g., senior or junior clinician), clinician disabilities, and/or other preferences described herein. In some implementations, the user notification configuration includes (824) one or more of color pallet, audio tone, audio rate, and audio pitch.

In some implementations, the method 800 includes presenting (826) at least one human perceivable manifestations of another notification to the user. The at least one human perceivable manifestation of the other notification is generated by a distinct medical device associated with the user 210. More specifically, in some implementations, the method includes presenting one or more manifestations of notifications from more than one medical device for the user 210. For example, a first PCD 12 may present one or more manifestations of a first notification and a second PCD 12 may present one or more manifestations of a second notification, a user who is currently operating the first PCD 12 may be presented with one or more manifestations for both the first and second notifications (at the first PCD 12). In some implementations, the distinct medical device is in proximity to the medical device, and in response to the determination that the authentication request was received from the user, adjusting (828) presentation of the at least one human perceivable manifestations of the other notification for the predetermined period of time. For example, continuing the example above, if the second PCD 12 is in proximity to the first PCD 12, at least one manifestation of the second notification may be adjusted for the predetermined period of time.

Figure 9:
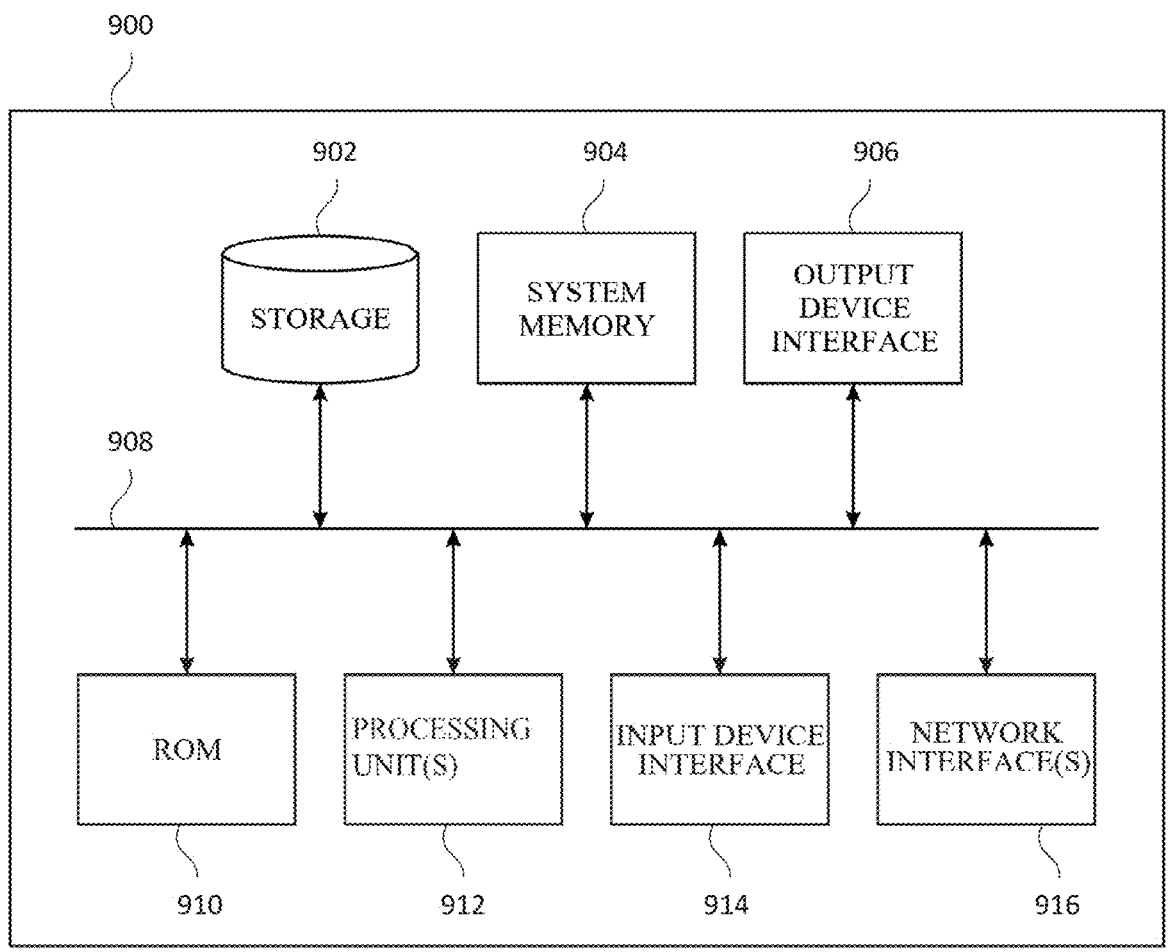
FIG. 9 is a conceptual diagram illustrating an example electronic system for implementing an alarm management system, according to various aspects of the subject technology.

FIG. 9 is a conceptual diagram illustrating an example electronic system 900 for implementing an alarm management system, according to various aspects of the subject technology. Electronic system 900 may be a computing device for execution of software associated with one or more portions or steps of process 800, or components and processes provided by FIGS. 1-8. Electronic system 900 may be representative, in combination with the disclosure regarding FIGS. 1-5, of the alarm management system described above. In this regard, electronic system 900 may be a microcomputer, personal computer, or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 900 may include various types of computer readable media and interfaces for various other types of computer readable media. In the depicted example, electronic system 900 includes a bus 908, processing unit(s) 912, a system memory 904, a read-only memory (ROM) 910, a permanent storage device 902, an input device interface 914, an output device interface 906, and one or more network interfaces 916. In some implementations, electronic system 900 may include or be integrated with other computing devices or circuitry for operation of the various components and processes previously described.

Bus 908 collectively represents all system, peripheral, and chipset buses that communicatively connect the numerous internal devices of electronic system 900. For instance, bus 908 communicatively connects processing unit(s) 912 with ROM 910, system memory 904, and permanent storage device 902.

From these various memory units, processing unit(s) 912 retrieves instructions to execute and data to process in order to execute the processes of the subject disclosure. The processing unit(s) can be a single processor or a multi-core processor in different implementations.

ROM 910 stores static data and instructions that are needed by processing unit(s) 912 and other modules of the electronic system. Permanent storage device 902, on the other hand, is a read-and-write memory device. This device is a non-volatile memory unit that stores instructions and data even when electronic system 900 is off. Some implementations of the subject disclosure use a mass-storage device (such as a magnetic or optical disk and its corresponding disk drive) as permanent storage device 902.

Some implementations use a removable storage device (such as a floppy disk, flash drive, and its corresponding disk drive) as permanent storage device 902. Like permanent storage device 902, system memory 904 is a read-and-write memory device. However, unlike storage device 902, system memory 904 is a volatile read-and-write memory, such a random-access memory. System memory 904 stores some of the instructions and data that the processor needs at runtime. In some implementations, the processes of the subject disclosure are stored in system memory 904, permanent storage device 902, and/or ROM 910. From these various memory units, processing unit(s) 912 retrieves instructions to execute and data to process in order to execute the processes of some implementations.

Bus 908 also connects to input and output device interfaces 914 and 906. Input device interface 914 enables the user to communicate information and select commands to the electronic system. Input devices used with input device interface 914 include, e.g., alphanumeric keyboards and pointing devices (also called "cursor control devices"). Output device interfaces 906 enables, e.g., the display of images generated by the electronic system 900. Output devices used with output device interface 906 include, e.g., printers and display devices, such as cathode ray tubes (CRT) or liquid crystal displays (LCD). Some implementations include devices such as a touchscreen that functions as both input and output devices.

Also, bus 908 also couples electronic system 900 to a network (not shown) through network interfaces 916. Network interfaces 916 may include, e.g., a wireless access point (e.g., Bluetooth or WiFi) or radio circuitry for connecting to a wireless access point. Network interfaces 916 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 900 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, audible feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML, page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any implementation, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Aspects described include artificial intelligence or other operations whereby the system processes inputs and generates outputs with apparent intelligence. For example, the predetermined period of time for adjusting manifestations of a notification may be based on the users 210 response times. In another example, sleep patterns, sensitivity to manifestation types, and/or other patient specific information can be recognized via the inputs, and adjustments to the manifestations of a notification may be based on the recognized patterns. The artificial intelligence may be implemented in whole or in part by a model. A model may be implemented as a machine learning model. The learning may be supervised, unsupervised, reinforced, or a hybrid learning whereby multiple learning techniques are employed to generate the model. The learning may be performed as part of training. Training the model may include obtaining a set of training data and adjusting characteristics of the model to obtain a desired model output. For example, three characteristics may be associated with a desired item location. In such instance, the training may include receiving the three characteristics as inputs to the model and adjusting the characteristics of the model such that for each set of three characteristics, the output device state matches the desired device state associated with the historical data.

In some implementations, the training may be dynamic. For example, the system may update the model using a set of events. The detectable properties from the events may be used to adjust the model.

The model may be an equation, artificial neural network, recurrent neural network, convolutional neural network, decision tree, or other machine-readable artificial intelligence structure. The characteristics of the structure available for adjusting during training may vary based on the model selected. For example, if a neural network is the selected model, characteristics may include input elements, network layers, node density, node activation thresholds, weights between nodes, input or output value weights, or the like. If the model is implemented as an equation (e.g., regression), the characteristics may include weights for the input parameters, thresholds or limits for evaluating an output value, or criterion for selecting from a set of equations.

Once a model is trained, retraining may be included to refine or update the model to reflect additional data or specific operational conditions. The retraining may be based on one or more signals detected by a device described herein or as part of a method described herein. Upon detection of the designated signals, the system may activate a training process to adjust the model as described.

Further examples of machine learning and modeling features which may be included in the implementations discussed above are described in "A survey of machine learning for big data processing" by Qiu et al. in EURASIP Journal on Advances in Signal Processing (2016) which is hereby incorporated by reference in its entirety.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A medical device for reducing generated alarm strain, the medical device comprising:
   a display to present visually perceivable information;
   an audio output to present audibly perceivable information;
   one or more processors coupled with the display and the audio output; and
   memory storing one or more instructions that, when executed by the one or more processors, cause the medical device to perform operations including:
      generating a notification regarding the medical device, wherein the notification is associated with an audible manifestation and a visual manifestation;
      detecting that a user is focused on the medical device, wherein detecting that the user is focused on the medical device is based on authenticating the user to the medical device or detecting user interaction via the medical device;
      after said detection of the user, determining a volume adjustment to the audio output for presenting the audible manifestation; and
      adjusting the audio output to cause presentation of the audible manifestations according to the volume adjustment, wherein the audio output presents the audible manifestation with the volume adjustment at a lower volume than the audio output would present the audible manifestation without the volume adjustment;
      presenting at least one other audible manifestation and at least one other visual manifestation of another notification to the user, the at least one other audible manifestation and at least one other visual manifestation of the other notification being generated by a distinct medical device associated with the user and in proximity to the medical device, and
      adjusting the at least one other audible manifestation and at least one other visual manifestation of the other notification in response to receiving an authentication request from the user via the medical device.

2. A method for reducing alarm strain generated by a medical device, comprising:
   at the medical device:
      generating a notification regarding the medical device, wherein the notification is associated with at least two human perceivable manifestations;
      detecting that a user is focused on the medical device, wherein detecting that the user is focused on the medical device is based on authenticating the user to the medical device or detecting user interaction via the medical device;
      determining one or more adjustments to at least one of the human perceivable manifestation of the notification, the determined one or more adjustments based at least in part on said detecting; and
      adjusting presentation of the at least one of the human perceivable manifestations of the notification for a predetermined period of time, the adjusted presentation based at least in part on the determined one or more adjustments;
      presenting at least one human perceivable manifestation of another notification to the user, the at least one human perceivable manifestation of the other notification being generated by a distinct medical device associated with the user and in proximity to the medical device, and
      adjusting the at least one human perceivable manifestation of the other notification in response to receiving an authentication request from the user via the medical device.

3. The method of claim 2, wherein detecting that the user is focused on the medical device includes detecting a user identifier in proximity to the medical device, and automatically receiving credentials of the user via an electronic device associated with the user.

4. The method of claim 3, wherein in proximity to the medical device includes contacting the medical device.

5. The method of claim 3, wherein detecting the user identifier in proximity to the medical device includes a one-foot detection radius around the medical device.

6. The method of claim 2, wherein the at least one human perceivable manifestations of the other notification is adjusted for the predetermined period of time.

7. The method of claim 2, wherein the predetermined period of time is at least 30 seconds.

8. The method of claim 2, wherein the medical device is an infusion pump, and the method further comprises:
   dynamically determining the predetermined period of time based, in part, on a drug being infused, alarm type, user preference, whether user is logged into the infusion pump, whether infusion pump is locked, and/or user proximity to the infusion pump.

9. The method of claim 2, wherein adjusting presentation, by the medical device, of the at least one of the human perceivable manifestations of the notification for the predetermined period of time includes silencing an audible manifestation of the notification and/or temporarily dismissing a visual manifestation of the notification.

10. The method of claim 2, wherein the method further comprises:
    detecting an environmental condition within proximity of the medical device; and
    the determined one or more adjustments are based at least in part on a detected environmental condition,
    wherein the environmental condition includes one or more of time, light level, noise level, temperature, number of pumping modules associated with the medical device, patient information, patient monitoring data, and medical device location.

11. The method of claim 2, wherein the method further comprises:
    retrieving a user notification configuration from a data storage device, wherein the retrieval is based at least in part on a portion of authentication information received by the medical device for the user; and
    the determined one or more adjustments are based at least in part on the user notification configuration.

12. The method of claim 11, wherein the user notification configuration includes one or more of color pallet, audio tone, audio rate, audio volume, and audio pitch.

13. A non-transitory computer readable medium storing one or more programs, the one or more programs comprising instructions, which when executed by a medical device, cause the medical device to:
    generate a notification regarding the medical device, wherein the notification is associated with at least two human perceivable manifestations;
    detect that a user is focused on the medical device, wherein detecting that the user is focused on the medical device is based on authenticating the user to the medical device or detecting user interaction via the medical device;

determine one or more adjustments to at least one of the human perceivable manifestation of the notification, a determined one or more adjustments based at least in part on said detecting; and adjust presentation of the at least one of the human perceivable manifestations of the notification for a predetermined period of time, the adjusted presentation based at least in part on the determined one or more adjustments;

present at least one human perceivable manifestation of another notification to the user, the at least one human perceivable manifestation of the other notification being generated by a distinct medical device associated with the user and in proximity to the medical device, and adjust the at least one human perceivable manifestation of the other notification in response to receiving an authentication request from the user via the medical device.

14. The non-transitory computer readable medium of claim 13, wherein adjusting presentation, by the medical device, of the at least one of the human perceivable manifestations of the notification for the predetermined period of time includes silencing an audible manifestation of the notification and/or temporarily dismissing a visual manifestation of the notification.

15. The non-transitory computer readable medium of claim 13, wherein detecting that the user is focused on the medical device includes detecting a user identifier in proximity to the medical device, and automatically receiving credentials of the user via an electronic device associated with the user.

16. The non-transitory computer readable medium of claim 13, further comprising instructions, which when executed by the medical device, cause the medical device to:
    detect an environmental condition within proximity of the medical device; and
    the determined one or more adjustments are based at least in part on a detected environmental condition.

17. The non-transitory computer readable medium of claim 13, further comprising instructions, which when executed by the medical device, cause the medical device to:
    retrieve a user notification configuration from a data storage device, wherein the retrieval is based at least in part on a portion of authentication information received by the medical device for the user; and
    the determined one or more adjustments are based at least in part on the user notification configuration.

18. The non-transitory computer readable medium of claim 13, further comprising instructions, which when executed by the medical device, cause the medical device to:
    activate a control element of the medical device for acknowledging the notification, said activation of the control element based at least in part on said detecting; and
    upon activation of the control element, adjust the presentation of the at least one of the human perceivable manifestations of the notification.

19. The non-transitory computer readable medium of claim 13, further comprising instructions, which when executed by the medical device, cause the medical device to receive a parameter to control delivery of a fluid via the medical device, and wherein the user interaction includes receiving the parameter.

* * * * *